US009402820B2

(12) United States Patent
Matsumoto et al.

(10) Patent No.: US 9,402,820 B2
(45) Date of Patent: Aug. 2, 2016

(54) USE OF PYRUVATE OR SUCCINATE TO ENHANCE THE EFFICACY OF A HYPOXIA ACTIVATED PRODRUG FOR THE TREATMENT OF TUMORS

(75) Inventors: Shingo Matsumoto, Rockville, MD (US); Robert J. Gillies, Tampa, FL (US); James B. Mitchell, Damascus, MD (US); Murali K. Cherukuri, Rockville, MD (US); Keita Saito, Silver Spring, MD (US)

(73) Assignees: THE UNITED STATES OF AMERICA AS REPRESENTED BY THE SECRETARY, DEPARTMENT OF HEALTH AND HUMAN SERVICES, Washington, DC (US); H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 42 days.

(21) Appl. No.: 14/112,906

(22) PCT Filed: Apr. 20, 2012

(86) PCT No.: PCT/US2012/034534

§ 371 (c)(1), (2), (4) Date: Oct. 18, 2013

(87) PCT Pub. No.: WO2012/145684

PCT Pub. Date: Oct. 26, 2012

(65) Prior Publication Data

US 2014/0045796 A1 Feb. 13, 2014

Related U.S. Application Data

(60) Provisional application No. 61/478,465, filed on Apr. 22, 2011.

(51) Int. Cl.

| | |
|---|---|
| ***A61K 31/19*** | (2006.01) |
| ***A61K 45/06*** | (2006.01) |
| ***A61K 31/355*** | (2006.01) |

(52) U.S. Cl.

CPC ............... *A61K 31/19* (2013.01); *A61K 31/355* (2013.01); *A61K 45/06* (2013.01)

(58) Field of Classification Search

None

See application file for complete search history.

(56) References Cited

U.S. PATENT DOCUMENTS

| | | |
|---|---|---|
| 4,734,276 A | 3/1988 | Ziegler |
| 5,646,185 A | 7/1997 | Giaccia et al. |

(Continued)

FOREIGN PATENT DOCUMENTS

| | | |
|---|---|---|
| WO | WO 2004/087075 A2 | 10/2004 |
| WO | WO 2005/094236 A2 | 10/2005 |

(Continued)

OTHER PUBLICATIONS

Hockel et al. Tumor hypoxia: Definitions and current clinical, biologic and molecular aspects. Journal of National Cancer Institute, 2001, 93(4): 266-276.*

(Continued)

*Primary Examiner* — Anna Pagonakis

(74) *Attorney, Agent, or Firm* — Klarquist Sparkman, LLP

(57) ABSTRACT

The identification of $pO_2$ lowering agents as transient hypoxia-inducers is disclosed herein. Provided is a method of enhancing the efficacy of a hypoxia-sensitive agent in a subject, by administering to the subject a therapeutically effective amount of the hypoxia-sensitive agent and a therapeutically effective amount of a $pO_2$ lowering agent. Methods of treating a subject with a tumor, by administering to the subject a therapeutically effective amount of a $pO_2$ lowering agent and a therapeutically effective amount of a hypoxia-sensitive agent are also disclosed.

17 Claims, 10 Drawing Sheets

(56) References Cited

U.S. PATENT DOCUMENTS

| | | | |
|---|---|---|---|
| 6,086,789 | A | 7/2000 | Brunengraber et al. |
| 6,797,820 | B2 | 9/2004 | Patel et al. |
| 7,448,389 | B1 | 11/2008 | Kotha et al. |
| 7,547,673 | B2 | 6/2009 | Ko et al. |
| 2003/0013656 | A1 | 1/2003 | Wang et al. |
| 2007/0212360 | A1 | 9/2007 | Denko et al. |
| 2009/0209618 | A1 | 8/2009 | Dang et al. |

FOREIGN PATENT DOCUMENTS

| | | | |
|---|---|---|---|
| WO | WO 2005/094236 | A3 | 10/2005 |
| WO | WO 2005/094236 | A9 | 10/2005 |
| WO | WO 2007/002931 | * | 1/2007 |
| WO | WO 2008/076964 | A1 | 6/2008 |
| WO | WO 2009/126705 | A2 | 10/2009 |

OTHER PUBLICATIONS

Bromopyruvic acid—Wikipedia, the free encyclopedia: http://en.wikipedia.org/wiki/Bromopyruvic_acid (3 pages) (printed on Mar. 26, 2015).

Glycolysis: "Glycolysis, Krebs Cycle, and other Energy-Releasing Pathways," http://www.uic.edu/classes/bios/bios100/lectures/respiration.htm (7 pages) (printed on Mar. 26, 2015).

Ihrlund et al., "3-Bromopyruvate as Inhibitor of Tumour Cell Energy Metabolism and Chemopotentiator of Platinum Drugs," *Molecular Oncology* 2:94-101 (2008).

Komi et al., "Inhibition of Tumor Angiogenesis by Targeting Endothelial Surface ATP Synthase with Sangivamycin," *Jpn. J. Clin. Oncol.* 37(11)867-873 (2007).

Pyruvic acid—Wikipedia, the free encyclopedia: http://en.wikipedia.org/wiki/Pyruvic_acid (7 pages) (printed on Mar. 26, 2015).

Wilson and Hay, "Targeting Hypoxia in Cancer Therapy," *Nature Reviews* 11:393-410 (Jun. 2011).

Brown, "Exploiting the hypoxic cancer cell: mechanisms and therapeutic strategies," Molecular Medicine Today 6:157-162 (Apr. 2000).

Cairns et al., "Metabolic targeting of hypoxia and HIF1 in solid tumors can enhance cytotoxic chemotherapy," PNAS 104(22):9445-9450 (May 29, 2007).

Golman et al., Metabolic imaging by hyperpolarized 13C magnetic resonance imaging for in vivo tumor diagnosis, Cancer Res 66(22):10855-10860 (Nov. 15, 2006).

Hara, "Studies on the isomer and succinic acid II. Anticancer activity of the isomer of succinic acid," The Japanese Journal of Veterinary Science 29(3):117-131 (Jun. 1967).

International Search Report and Written Opinion from parent PCT Application No. PCT/US2012/034534, 13 pages (mailed Aug. 2, 2012).

Liang et al., "Ethyl pyruvate administration inhibits hepatic tumor growth," *Journal of Leukocyte Biology* 86:599-607 (2009).

Patterson and McKeown, AQ4N: a new approach to hypoxia-activated cancer chemotherapy, British Journal of Cancer 83(12):1589-1593 (2000).

Perrin et al., "Pyruvate reverses metabolic effects produced by hypoxia in glioma and hepatoma cell cultures," *Biochimie* 84(10)1003-1011 (Oct. 2002) (Abstract only).

Ren et al., "A novel specific application of pyruvate protects the mouse retina against white light damage: differential stabilization of HIF-1α and HIF-2α," *Manuscript 10-5605 IOVS* 19 pages (Jan. 12, 2011).

Roudier et al., "Considering the role of pyruvate in tumor cells during hypoxia," BBA—Reviews on Cancer 1796(2):55-62 (Dec. 1, 2009).

Roudier et al., "Pyruvate reduces DNA damage during hypoxia and after reoxygenation in hepatocellular carcinoma cells," *FEBS Journal* 274:5188-5198 (2007).

Saito et al., "Transient decrease on tumor oxygenation after intravenous administration of pyruvate," *Magnetic Resonance in Medicine* 67:801-807 (2012).

* cited by examiner

USE OF PYRUVATE OR SUCCINATE TO ENHANCE THE EFFICACY OF A HYPOXIA ACTIVATED PRODRUG FOR THE TREATMENT OF TUMORS

CROSS REFERENCE TO RELATED APPLICATION

This is the U.S. national stage of PCT Application No. PCT/US2012/034534, filed Apr. 20, 2012, which was published in English under PCT Article 21(2), which application claims the benefit of U.S. Provisional Application No. 61/478,465, filed Apr. 22, 2011, which is incorporated herein by reference.

ACKNOWLEDGMENT OF GOVERNMENT SUPPORT

This invention was made with government support under NIH R01 grant CA 125627 awarded by the Department of Health and Human Services. The United States government has certain rights in the invention.

FIELD OF THE DISCLOSURE

This disclosure concerns agents that transiently decrease the partial pressure of oxygen in a tumor and methods of using them to increase the efficacy of hypoxia-sensitive agents to treat subjects with a tumor.

BACKGROUND

Hypoxia within regions of solid tumors is associated with resistance to standard treatments, particularly radiotherapy. The hypoxia occurs in part because the tumor's vasculature is highly unordered and leaves significant portions of the tumor unperfused. Conventional drug therapy, which depends on reaching the cancer through the bloodstream, can be less effective in hypoxic tumors.

Drug designers have taken advantage of the hypoxic regions in tumors and designed anticancer drugs that are specifically active or activated under hypoxic conditions. For example, hypoxia-activated prodrugs are chemically modified to be inactive, but when administered to the body and exposed to hypoxic conditions (such as in a tumor), they are metabolized or otherwise converted into the active, anticancer form. Despite these new drugs, there is an ongoing need for innovative approaches to anticancer therapy.

SUMMARY OF THE DISCLOSURE

It is surprisingly disclosed herein that tumor cell oxygen partial pressure ($pO_2$) can be transiently decreased by exogenous administration of an agent that induces hypoxia in the tumor. Thus, provided herein is a method of enhancing the efficacy of a hypoxia-sensitive agent in a subject by administering to the subject a therapeutically effective amount of a hypoxia-sensitive agent and a therapeutically effective amount of a $pO_2$ lowering agent, wherein the amount of $pO_2$ lowering agent administered is sufficient to transiently enhance hypoxia of the tumor, thereby enhancing the efficacy of the hypoxia-sensitive agent. Also provided is a method of treating a subject with a tumor by administering to the subject a therapeutically effective amount of a hypoxia-sensitive agent and a therapeutically effective amount of a $pO_2$ lowering agent in an amount sufficient to transiently enhance hypoxia of the tumor. Further provided is a method of inducing hypoxia in a tumor cell, comprising administering to a subject with a tumor an unlabeled mitochondrial substrate, wherein the amount of the unlabeled mitochondrial substrate is sufficient to transiently induce hypoxia of the tumor cell.

The foregoing and other features and advantages of the invention will become more apparent from the following detailed description of a several embodiments which proceeds with reference to the accompanying figures.

BRIEF DESCRIPTION OF THE FIGURES

FIGS. 1A and 1B both show $T_2$ weighted (T2W) anatomical images of a representative squamous cell sarcoma (SCC) tumor-bearing mouse, and the corresponding partial pressure of oxygen ($pO_2$) maps. FIG. 1A shows a control tumor which did not receive [1-$^{13}$C]pyruvate injection. FIG. 1B shows a tumor measured after administration of hyperpolarized [1-$^{13}$C]pyruvate. FIG. 1C shows the median $pO_2$ in tumors with and without [1-$^{13}$C]pyruvate administration (n=4). FIG. 1D shows the percentage of the hypoxic region in tumors with and without [1-$^{13}$C]pyruvate administration (n=4).

FIG. 2A shows $T_2$-weighted anatomical images of a representative SCC tumor-bearing mouse, and the corresponding $pO_2$ maps measured before, or 30 minutes, 1 hour, and 5 hours after, [1-$^{13}$C]pyruvate injection. The adjacent center three slices of the 3D images were displayed, and every slice is 2 mm in thickness (S6=slice 6; S7=slice 7; S8=slice 8). $pO_2$ levels (0-60 mm Hg) in the tumors are correlated with shades of grey. FIG. 2B shows a frequency histogram of the tumor $pO_2$ shown in (A) before (black) and 30 minutes after (grey) pyruvate injection. FIG. 2C shows the median $pO_2$ in tumors (n=4). FIG. 2D shows the percentage of the hypoxic region ($pO_2$<10 mmHg) in tumors (n=4). *$P<0.01$, **$P<0.05$, compared with before pyruvate injection.

FIG. 3A shows the immunostaining of hypoxia marker pimonidazole (Pimo) in representative tumors of control mice and pyruvate-treated mice (1 hour and 5 hours after [1-$^{13}$C]pyruvate injection). FIG. 3B quantifies the pimonidazole positive area (n=5).

FIG. 5A shows $T_2$-weighted (T2W) anatomical images of three representative human pancreatic tumor-bearing mice, and the corresponding $pO_2$ maps measured before (pre), or 10 minutes, 30 minutes, and 1 hour after, [1-$^{13}$C]pyruvate injection (1.15 mmol/kg i.v.). $pO_2$ levels (0-60 mm Hg) in the tumors are correlated with shades of grey. FIG. 5B shows the effect of pyruvate on tumor $pO_2$ (n=5-6). FIG. 5C shows the effect of pyruvate on the hypoxic fraction (HF; $pO_2$<10 mmHg) in tumors (n=5-6).

FIG. 6A shows the effect on SCCVII-bearing C3H mice of intraperitoneal (i.p.) dosing of TH-302 (100 mg/kg) alone or in combination with intravenous (i.v.) injection of pyruvate (1.15 mmol/kg). Pyruvate is administered 30 minutes prior to TH-302 dosing. FIG. 6B shows the effect on HT29-bearing nude mice of intraperitoneal (i.p.) dosing of TH-302 (100 mg/kg) alone or in combination with intravenous (i.v.) injection of pyruvate (1.15 mmol/kg). Pyruvate is administered 30 minutes prior to TH-302 dosing. * denotes days of drug dosing.

FIG. 7A shows oxygen consumption rate (OCR) in SCCVII cells following incubation with various concentrations of pyruvate for 21 minutes. Data represent the percent change of OCR from baseline measurements. FIG. 7B shows the OCR in SCCVII cells treated with Rotenone/Antimycin A (oxidative phosphorylation complex 1 and complex 3 inhibitors, respectively) following 2 mM pyruvate treatment. FIG. 7C shows the OCR in SCCVII cells treated with Rotenone/Antimycin A prior to 2 mM pyruvate treatment.

DETAILED DESCRIPTION OF SEVERAL EMBODIMENTS

I. Abbreviations

Figures 1A, 1B, 1C, 1D:
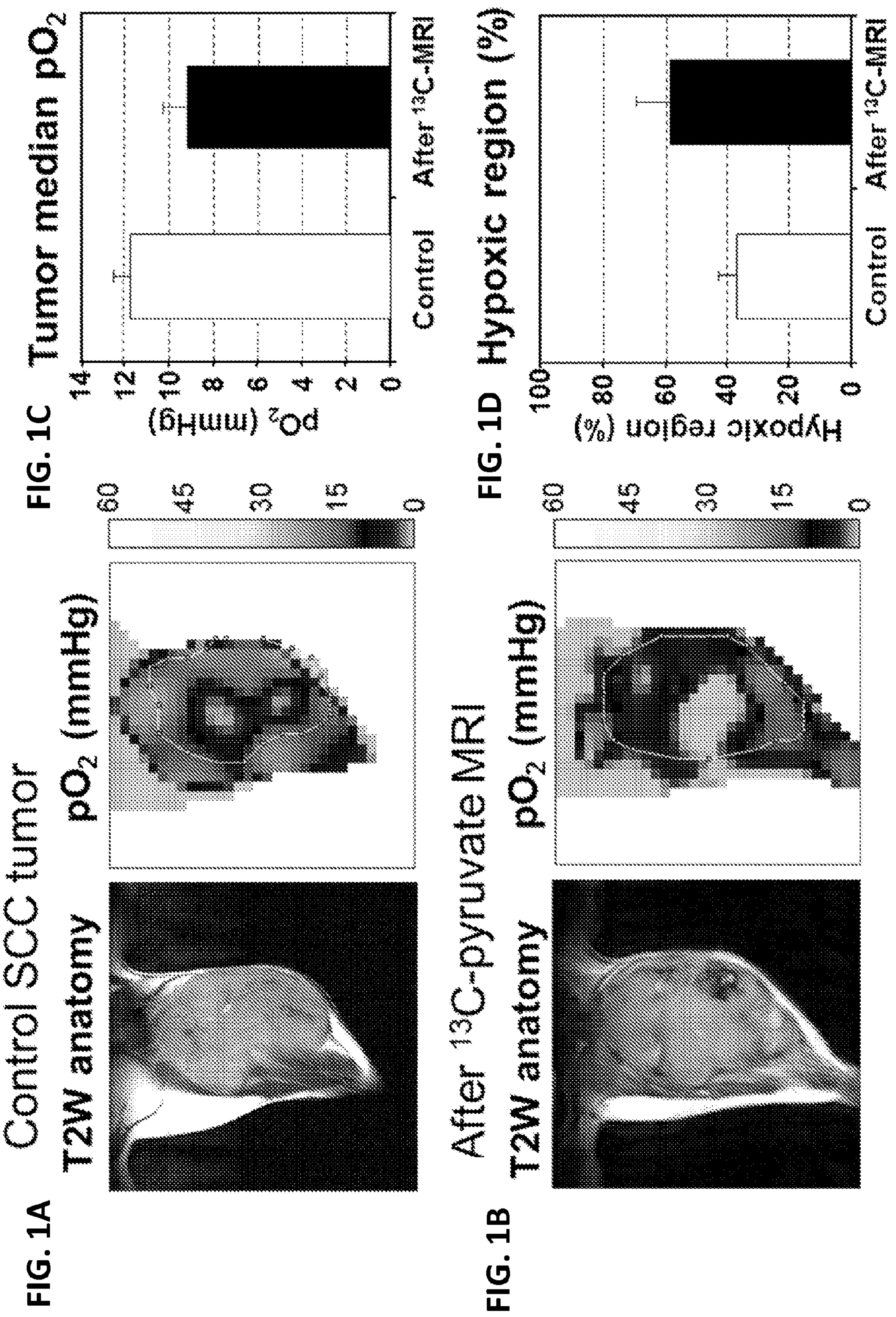
FIGS. 1A-1D are a series of digital images and graphs showing the comparison of tumor $pO_2$ between tissues treated "with" and "without" hyperpolarized [1-$^{13}$C]pyruvate.

CNS Central nervous system
EPR Electron paramagnetic resonance
EPRI Electron paramagnetic resonance imaging
FLASH Fast low-angle shot
HAP Hypoxia-activated prodrug
HF Hypoxic fraction
i.p. Intraperitoneal
i.v. Intravenous
LDH Lactate dehydrogenase
MR Magnetic resonance
MRI Magnetic resonance imaging
NMR Nuclear magnetic resonance
OCR Oxygen consumption rate
$pO_2$ Partial pressure of oxygen
SCC Squamous cell sarcoma
SPI Single-point imaging
TAM Triarylmethyl
TCA Tricarboxylic acid

II. Terms

Unless otherwise noted, technical terms are used according to conventional usage. Definitions of common terms in molecular biology may be found in Benjamin Lewin, *Genes IX*, published by Jones and Bartlett Publishers, 2007 (ISBN 0763740632); Kendrew et al. (eds.), *The Encyclopedia of Molecular Biology*, published by Blackwell Science Inc., 1998; and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: The introduction of a composition into a subject by a chosen route. For example, if the chosen route is intravenous, the composition is administered by introducing the composition into a vein of the subject. In another example, the administration can be anatomically targeted, for example by infusion into an artery perfusing a target area, such as an organ. In particular examples, the infusion is performed selectively into the arterial supply of a tumor, for example into a hepatic artery to treat a liver tumor, or into the vertebral or cerebral artery to treat a brain tumor.

Anti-angiogenic agent: An agent that disrupts angiogenesis and prevents the formation of blood vessels. Examples of anti-angiogenic agents include bevacizumab, sorafenib, and sunitinib.

Antibody: A polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions of antibodies well known in the art, such as Fab fragments, Fab' fragments, $F(ab)'_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* $3^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Binding partner: Any molecule or composition capable of recognizing and specifically binding to a defined structural aspect of another molecule or composition. Examples of such binding partners and corresponding molecule or composition include biotin/avidin (such as biotin/streptavidin), antigen/antibody, hapten/antibody, and lectin/carbohydrate.

Bioreductive agent: Compound or drug that accepts electrons in an oxidation-reduction reaction. Bioreductive agents exhibit a high specificity for hypoxic cells under conditions of low oxygen partial pressures (for example, at 10%, 2%, 0.2%, or 0.02% oxygen). These agents can be bioactivated under hypoxic conditions via one-electron reduction to a highly reactive free radical intermediate that generates a hydroxyl ion to fragment DNA.

Bioreductive prodrugs show minimal toxicity in normoxic cells. In hypoxic cells, they are converted, for example by an enzymatic process (which is inhibited by oxygen), to a stable persistent cytotoxin. The product binds non-covalently to DNA with an affinity high enough to produce cytotoxicity and low enough to allow slow diffusion and subsequent cytotoxicity in proximate tumor cells irrespective of their oxygen levels.

The response of tumors to bioreductive agents not only depends on the tumor oxygenation but also on reductive enzymes within the tumor that are necessary to bioactivate the drug to a DNA-damaging species. Therefore, tumor variability in bioreductive capacity, both in terms of hypoxic fraction and enzyme profile, will determine response and therapeutic outcome.

Chemotherapeutic agent: An agent with therapeutic usefulness in the treatment of diseases characterized by abnormal cell growth or hyperplasia. Such diseases include cancer, as well as diseases characterized by hyperplastic growth such as psoriasis. One of skill in the art can readily identify a chemotherapeutic agent (for instance, see Slapak and Kufe, *Principles of Cancer Therapy*, Chapter 86 in *Harrison's Principles of Internal Medicine,* 14th edition; Perry et al., *Chemotherapy*, Ch. 17 in Abeloff, *Clinical Oncology* $2^{nd}$ ed., © 2000 Churchill Livingstone, Inc; Baltzer L, Berkery R (eds): *Oncology Pocket Guide to Chemotherapy,* 2nd ed. St. Louis, Mosby-Year Book, 1995; Fischer D S, Knobf M F, Durivage H J (eds): *The Cancer Chemotherapy Handbook*, 4th ed. St. Louis, Mosby-Year Book, 1993).

Examples of anti-tumor chemotherapeutic agents that could be used in the methods disclosed herein include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechloretliamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl. 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELB E® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluorometihylomithine (DMFO); retinoids such as retinoic acid; capecitabine; combretastatin; leucovorin (LV); oxaliplatin, including the oxaliplatin treatment regimen (FOLFOX); inhibitors of PKC-alpha, Raf, H-Ras, EGFR (e.g., erlotinib (Tarceva™)) and VEGF-A that reduce cell proliferation and pharmaceutically acceptable salts, acids or derivatives of any of the above.

Also included are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in aberrant cell proliferation, such as, for example, PKC-alpha, Raf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; Vinorelbine and Esperamicins (see U.S. Pat. No. 4,675,187); and pharmaceutically acceptable salts, acids or derivatives of any of the above.

Chemotherapeutic drugs also include hypoxia-sensitive agents, such as a hypoxia-activated drug or a hypoxia-activated prodrug. Specific, non-limiting examples of a hypoxia-activated prodrug include banoxantrone (AQ4N; NSC 673504; Novacea Inc.), PR-104 (Proacta Inc.), tirapazamine (SR4223), and TH-302 (Threshold Pharmaceuticals, Inc.). Specific, non-limiting examples of a hypoxia-activated drug include mitomycin C and 3-bromopyruvate.

Co-administration (co-administering): Administration of a first agent (for example, pyruvate) with a second agent (for example, a hypoxia-sensitive agent) within the same general time period, and does not require administration at the same exact moment in time (although co-administration is inclusive of administering at the same exact moment in time). Thus, co-administration may be on the same day or on different days, or in the same week or in different weeks. Two, three, four, or more agents can be co-administered. The co-administered agents may be included in the same composition or they may each individually be included in separate compositions. However, the two agents are administered during a time frame wherein their respective periods of biological activity overlap. Thus, the term includes sequential as well as co-extensive administration of two or more agents.

Cytotoxicity: The quality of being toxic to a cell. A "cytotoxic agent," as used herein, refers to a substance that inhibits or prevents the function of cells, prevents the proliferation and/or growth of cells, and/or causes the destruction (killing) of cells. The term is intended to include radioactive isotopes (e.g., $I^{131}$, $I^{125}$, $Y^{90}$ and $Re^{186}$), bioreductive agents, chemotherapeutic agents, and toxins such as enzymatically active toxins of bacterial, fungal, plant or animal origin, or fragments thereof.

DNA repair: A collection of processes by which a cell identifies and corrects damage to the DNA molecules that encode its genome. In human cells, both normal metabolic activities and environmental factors such as UV light can cause DNA damage, resulting in as many as 1 million individual molecular lesions per cell per day. Many of these lesions cause structural damage to the DNA molecule and can alter or eliminate the cell's ability to transcribe the gene that the affected DNA encodes. Other lesions induce potentially harmful mutations in the cell's genome. Consequently, the DNA repair process must be constantly active so it can respond rapidly to any damage in the DNA structure.

The rate of DNA repair is dependent on many factors, including the cell type, the age of the cell, and the extracellular environment. A cell that has accumulated a large amount of DNA damage, or one that no longer effectively repairs damage incurred to its DNA, can enter one of three possible states: an irreversible state of dormancy, known as senescence; apoptosis or programmed cell death or unregulated cell division, which can lead to the formation of a tumor that is cancerous.

Efficacy: Refers to the ability of agent to elicit a desired therapeutic effect. Efficacy also refers to the strength or effectiveness of a compound. As used herein, "enhancing efficacy" means to increase the therapeutic action (for example, the activity or beneficial result) of an agent. In one embodiment, when the agent is a hypoxia-sensitive agent, "enhancing efficacy" generally refers to increasing the ability of the agent to kill target cells, such as tumor cells (for example, increasing a chemotherapeutic, anti-proliferative, cytotoxic, or cell killing activity of a hypoxia-sensitive agent). Increasing the hypoxia level (or decreasing the partial pressure of oxygen), for example by the administration of a $pO_2$ lowering agent, can also enhance the efficacy of a hypoxia-sensitive agent.

Hyperproliferative disease: A disease or disorder characterized by the uncontrolled proliferation of cells. Hyperproliferative diseases include, but are not limited to non-malignant and malignant (cancer) tumors.

Hypoxia: A condition wherein the oxygen concentration is below normal levels for a particular tissue (such as a tumor). Hypoxia in a particular tissue as, compared to surrounding tissue, is referred to as relative tissue hypoxia. An example of relative tissue hypoxia is tumor hypoxia in which a tumor has lower levels of $pO_2$ than that of surrounding non-tumor tissue. In some examples of the disclosed methods, the level of oxygen is for example 10% or less (for example, 9%, 8%, 7%, 6%, 5%, 4%, 3%, 2%, or 1%), or for example 50 mmHg or less (for example, 45 mmHg, 40 mmHg, 35 mmHg, 30 mmHg, 25 mmHg, 20 mmHg, 15 mmHg, 10 mmHg, 5 mmHg, 4 mmHg, 3 mmHg, 2 mmHg, or 1 mmHg). The body as a whole (generalized hypoxia) or a region of the body (tissue hypoxia) may be deprived of adequate oxygen. Those of skill in the art would be familiar with the measurement of oxygen levels in biological systems and that oxygen measurements may be expressed in "mmHg," wherein, for example, 10% $O_2$ is equal to 76 mmHg and 1% $O_2$ is equal to 7.6 mmHg.

Transient hypoxia occurs when oxygen levels are below normal temporarily, followed by a return to normal oxygen levels. In one embodiment of the disclosed methods, transient hypoxia refers to decreased oxygen partial pressure levels (increased hypoxia) in a tumor after the administration of an agent, followed by the recovery to an oxygen partial pressure level equivalent to, or not statistically different from, the level before the administration of the agent.

Different levels of hypoxia in a tumor can occur at different time points, for example prior to and following administration of an agent that induces hypoxia (a hypoxia-inducer). Prior to administration of a hypoxia-inducer, a tumor already may be hypoxic but administration of a hypoxia-inducer further reduces the $pO_2$ level and therefore further increases hypoxia in the tumor, relative to non-tumor tissues or non-tumor cells surrounding the tumor. Different levels of hypoxia also can occur within a particular tumor. For example prior to administration of the agent a hypoxic tumor may be heterogeneously hypoxic, such that a tumor may be hypoxic, relative to non-tumor tissues or cells, in some regions of the tumor, but not hypoxic in other regions. Alternatively, a tumor may be variably hypoxic (exhibit various levels of hypoxia across the tumor tissue), compared to non-tumor tissues or cells. Administration of a hypoxia-inducer can induce hypoxia in the tumor such that a larger proportion or percentage of the tumor (for example, the entire tumor) is hypoxic, for example the tumor can become homogeneously hypoxic. The agent can affect (reduce $pO_2$ levels or increase hypoxia) of normoxic regions in a tumor, regions in a tumor that have not reached a threshold hypoxia, or all regions of a tumor regardless of their $pO_2$ (hypoxia) levels.

Hypoxia-activated prodrug (HAP): A bioreductive agent that is metabolized or otherwise converted into an activated form, with respect to a biological property, such as anti-tumor activity, in a hypoxic environment.

Hypoxia-inducer: An agent, such as a chemical compound, small molecule, or other composition (for example, an antisense compound, antibody, protease inhibitor, hormone, chemokine or cytokine), capable of initiating or increasing hypoxia (decreasing the oxygen partial pressure) in a tissue or in a subject. In some embodiments, the hypoxia-inducer causes transient hypoxia. In particular embodiments, the hypoxia-inducer is a mitochondrial substrate, for example pyruvate or succinate, which increases oxygen consumption in a cell. A hypoxia-inducer is also referred to as a $pO_2$ lowering agent.

Hypoxia-sensitive agent (hypoxic cytotoxin): An agent, such as a chemical compound, small molecule, or other composition (for example, an antisense compound, antibody, protease inhibitor, hormone, chemokine or cytokine), which has an altered activity under hypoxic conditions (hypoxia). The hypoxia-sensitive agent may have increased or decreased activity under hypoxic conditions. The hypoxia-sensitive agent can be a hypoxia-activated drug or a hypoxia-activated prodrug.

In some embodiments, the hypoxia-sensitive agent is inactive until exposed to hypoxic conditions (e.g. hypoxia-activated drugs). In particular embodiments, the hypoxia-sensitive agent is metabolized upon exposure to hypoxic conditions in order to be converted into the active form (e.g. hypoxia-activated prodrugs). Hypoxia-sensitive agents administered to a subject are capable of inducing a desired therapeutic or prophylactic effect when exposed to hypoxic conditions in a subject, for example in a hypoxic solid tumor in a subject. Hypoxia-sensitive agents can be administered in combination with agents that induce hypoxia (hypoxia-inducers, such as, for example pyruvate or succinate).

Examples of hypoxia-sensitive therapeutics include, inter alia, (i) hypoxia-activated prodrugs, for example, tirapazamine (TPZ; 3-amino-1,2,4-benzotriazine 1,4 dioxide; SR 4233), anthraquinone (AQ4N; Novacea), benzamidine (PR-104; 2-((2-bromoethyl)(2,4-dinitro-6-((2-(phosphonooxy)ethyl)carbamoyl)phenyl)amino)ethyl methanesulfonate; Proacta), and TH-302 (Threshold Pharmaceuticals, Inc.); and (ii) hypoxia-activated drugs, for example, mitomycin C, 3-bromopyruvate, and any drug that is more efficacious in hypoxic tumors. Additional examples of hypoxia-sensitive cytotoxins for use as anti-tumor agents include those disclosed in WO 2009/126,705 at pages 11-12, and the protein kinase C activators at column 2 of U.S. Pat. No. 5,646,185, both of which are incorporated by reference herein.

Isolated: An "isolated" biological component, such as a nucleic acid, protein or organelle that has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, nitorimidazoles, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

In some embodiments, the label is a fluorophore ("fluorescent label"). Fluorophores are chemical compounds, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ.

Mitochondrial substrate: Substrates of oxidative phosphorylation found in the mitochondria that stimulates activity of the mitochondria and reduces tissue $pO_2$ in cells to which the mitochondrial substrate is provided. Examples of mitochondrial substrates include small molecules (for example, pyruvate and succinate) and fatty acids. These are taken up as substrates in the citric acid cycle (also known as the tricarboxylic acid (TCA) cycle or Kreb's cycle) to promote cellular respiration. Cellular respiration consumes available cellular oxygen by converting oxygen into water at the end of the electron transport chain.

Neoplasia, malignancy, cancer and tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Malignant tumors are also referred to as "cancer."

Examples of solid tumors include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

Oligodeoxynucleotide: A nucleic acid molecule comprising deoxyribonucleotides (nucleotides with a deoxy sugar) and generally having a length of 300 bases or fewer.

Partial pressure: The individual pressure exerted independently by a particular gas within a mixture of gasses. The total pressure generated by the air is due in part to nitrogen, in part to oxygen, and in part to carbon dioxide. That part of the total pressure generated by oxygen is the 'partial pressure' of oxygen ($pO_2$), while that generated by carbon dioxide is the 'partial pressure' of carbon dioxide. A gas's partial pressure, therefore, is a measure of how much of that gas is present (e.g., in the blood or in a tissue). The partial pressure exerted by each gas in a mixture equals the total pressure times the fractional composition of the gas in the mixture. Partial pressure can be measured in atmospheres (atm), Pascals (Pa), percent of total gas, or mm of mercury (Hg). Normal partial pressure in the air is 760 mmHg (1 atmosphere [atm] of pressure=760 mmHg=101 kPa=15 lbs/square inch). As air is made up of 21% oxygen, the partial pressure of oxygen ($pO_2$) of dry air at sea level is approximately 159 mmHg.

The partial pressure of gases, such as oxygen, varies in different tissues of organisms since, for example, complex multicellular organisms will have certain tissues (respiring muscle) that use up oxygen, resulting in a lower partial pressure there. Blood returning to the heart from the tissues has a low $pO_2$ (40 mmHg). Oxygen diffuses from the high pressure in the alveoli (100 mmHg) to the area of lower pressure of the blood in the pulmonary capillaries (40 mmHg). In normal, subcutaneous tissue, the median $pO_2$ value is usually between 40 and 60 mmHg. Solid tumors are generally hypoxic (for example, less than 3 mmHg) because of inefficient delivery of oxygen to the tumor cells.

A partial pressure of oxygen lowering agent ("$pO_2$ lowering agent") refers to an agent that decreases $pO_2$ in a cell or tissue, such as a tumor cell or tumor tissue. Some such agents disclosed herein are selective $pO_2$ lowering agents in that they preferentially lower $pO_2$ in tumors as compared to non-tumor tissue, or they lower $pO_2$ without affecting the partial pressure of other gases in the cell or tissue, such as the partial pressure of $CO_2$ ($pCO_2$). Alternatively, the $pO_2$ lowering agent lowers $pO_2$ in both tumor and non-tumor tissue, however since tumor tissue is already hypoxic relative to non-tumor tissue, the $pO_2$ lowering agent preserves differential $pO_2$ between the tumor and non-tumor tissue.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as glycoproteins or amidated proteins. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Variant amino acid sequences may, for example, be 80, 90 or even 95 or 98% identical to the native amino acid sequence. Programs and algorithms for determining percentage identity can be found at the NCBI website.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide or small molecule preparation is one in which the oligonucleotide or small molecule is more pure than in an environment including a complex mixture of oligonucleotides or small molecules, respectively.

Pyruvate: The carboxylate (COOH) ion (anion) of pyruvic acid ($CH_3COCOO^-$), it is also known as 2-oxopropanoate, alpha-ketopropionate, acetylformate and pyroracemate. It is derived from glucose and is the end product of glycolysis. It can be converted to carbohydrates (such as glycogen) via gluconeogenesis, or to fatty acids through acetyl-CoA. It can also be used to construct the amino acid alanine and be converted into ethanol. Pyruvate (a reducing agent) is oxidized to acetyl-CoA and $CO_2$ by the pyruvate dehydrogenase complex (PDC) and acetyl-CoA enters the Krebs cycle (citric acid cycle or tricarboxylic acid cycle) when there is sufficient oxygen available. When the oxygen is insufficient, pyruvate is broken down anaerobically, creating lactate in animals (including humans) and ethanol in plants. In some embodiments, pyruvate decreases the partial pressure of oxygen in a tumor and is a hypoxia-inducer (or a $pO_2$ lowering agent). In other embodiments, pyruvate enhances the efficacy of a hypoxia-sensitive agent or enhances the region within a tissue, such as a tumor, that a hypoxia-sensitive agent is active.

Some of the methods disclosed herein use pyruvate as a substrate of mitochondrial respiration to decrease the $pO_2$ of tissues or cells to which the pyruvate is supplied. However, pyruvate analogs that also decrease cellular oxygen can be substituted for pyruvate. Examples of pyruvate analogs include, but are not limited to, pyruvate ester, pyruvate thioester, glycerol-pyruvate ester, dihydroxyacetone-pyruvate ester, oximes and amides of pyruvate, as well as L-lysine pyruvate and L-histidine pyruvate. The pyruvate may be administered as a free form (for example, as pyruvic acid) or as a salt, and in some embodiments it is the sole pharmacological moiety, i.e. it is not part of a larger molecule such as calcium pyruvate that has a pharmacological activity other than as a hypoxia-inducing agent.

Recombinant: A recombinant nucleic acid or polypeptide molecule is one that has a sequence that is not naturally occurring or has a sequence that is made by an artificial combination of two otherwise separated segments of sequence. This artificial combination can be accomplished by chemical synthesis of polypeptide or nucleic acid molecules, or by the artificial manipulation of isolated segments of nucleic acid molecules, such as by genetic engineering techniques.

Sample: Includes biological samples such as those derived from a human or other animal source (for example, blood, sweat, breast milk, bone marrow, stool, sera, urine, saliva, tears, biopsy samples, broncho-alevolar lavage fluids, histology tissue samples, cellular smears, moles, warts, body secretions etc.); bacterial or viral preparations; cell cultures; forensic samples; agricultural products; waste or drinking water; milk or other processed foodstuff; air; and so forth. A sample can contain genomic DNA, RNA, protein, or combinations thereof, obtained from a subject.

Sequence identity: The similarity between two nucleic acid sequences or between two amino acid sequences is expressed in terms of the level of sequence identity shared between the sequences. Sequence identity is typically expressed in terms of percentage identity; the higher the percentage, the more similar the two sequences.

Methods for aligning sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; Huang, et al., *Computer Applications in the Biosciences* 8:155-165, 1992; Pearson et al., *Methods in Molecular Biology* 24:307-331, 1994; Tatiana et al., (1999), *FEMS Microbiol. Lett.*, 174:247-250, 1999. Altschul et al. present a detailed consideration of sequence-alignment methods and homology calculations (*J. Mol. Biol.* 215:403-410, 1990).

The National Center for Biotechnology Information (NCBI) Basic Local Alignment Search Tool (BLAST™, Altschul et al. *J. Mol. Biol.* 215:403-410, 1990) is available from several sources, including the National Center for Biotechnology Information (NCBI, Bethesda, Md.) and on the Internet, for use in connection with the sequence-analysis programs blastp, blastn, blastx, tblastn and tblastx. A description of how to determine sequence identity using this program is available on the internet under the help section for BLAST™.

Small molecule: A molecule, typically with a molecular weight less than about 1000 Daltons, or in some embodiments, less than about 500 Daltons, wherein the molecule is capable of having an effect on cell metabolism, for example by modulating, to some measurable extent, an activity of a target molecule. Small molecule mitochondrial substrates of the citric acid cycle that stimulate mitochondrial respiration and lower cellular $pO_2$, such as pyruvate and succinate, have this activity and are small molecules.

Specific Binding Agent: An agent that binds substantially or preferentially only to a defined target, such as a protein, enzyme, polysaccharide, oligonucleotide, DNA, RNA, recombinant vector or a small molecule. Thus, a RNA-specific binding agent binds substantially only to the defined RNA, or to a specific region within the RNA. For example, a "specific binding agent" includes a siRNA that binds substantially to a specified RNA.

A protein-specific binding agent binds substantially only the defined protein, or to a specific region within the protein. For example, a "specific binding agent" includes antibodies and other agents that bind substantially to a specified polypeptide. The antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Subject: Living multi-cellular vertebrate organisms, a category that includes both human and veterinary subjects, including human and non-human mammals.

Substrate of mitochondrial respiration that increases cellular consumption of oxygen: A molecule upon which an enzyme of cellular respiration acts in the mitochondria. The substrates are primarily the substrates of the citric acid cycle, which are known to include oxaloacetate, citrate, cis-aconitate, isocitrate, oxalosuccinate, alpha-ketoglutarate, succinyl-CoA, succinate, fumarate and malate (L-malate). Metabolism of the substrate results in the release of electrons (hydrogen atoms), which are transferred to oxygen, resulting in the conversion of oxygen into water (consumption of oxygen). Under conditions where there is an increase in the metabolism of the mitochondrial substrate, either because of an increase in available substrate (for example, by the administration of pyruvate or succinate, such as the administration of a bolus of pyruvate or succinate) or an increase in the activity of the enzymes metabolizing the substrate, there is a concomitant increase in the release of electrons and conversion of oxygen into water (an increase in the consumption of oxygen). Thus, in particular embodiments of the methods disclosed herein, oxygen consumption in a cell or tissue (for example, a tumor) can be increased when the cells or tissue are exposed to an exogenous mitochondrial substrate or a source of the substrate, such as pyruvate or succinate (a $pO_2$ lowering agent).

Succinate: A dicarboxylic acid (also known as butanedioic acid or ethane-1,2-dicarboxylic acid) that plays a biochemical role in the citric acid cycle (Krebs cycle or tricarboxylic acid cycle). Succinate (a reducing agent) is capable of donating electrons to the electron transport chain and succinate can be converted to fumaric acid by oxidation. In some embodiments, succinate reduces the partial pressure of oxygen in a tumor and is a hypoxia inducer (or a $pO_2$ lowering agent). In other embodiments, succinate enhances the efficacy of a hypoxia-sensitive agent. However, succinate analogs that also decrease cellular oxygen can be substituted for succinate. An example of a succinate analog includes 3-sulfinopropionic acid. The succinate may be administered as a free form (for example, as succinic acid) or as a salt, and in some embodiments it is the sole pharmacological moiety, i.e. it is not part of a larger molecule, such as metoprolol succinate, that has a pharmacological activity other than as a hypoxia inducing agent.

Therapeutic or therapy: A treatment, referring to a prescribed course of action (including administration of therapeutic agents) to alter the normal course of a disorder.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject.

Therapeutically effective amount: A quantity of a specific substance sufficient to achieve a desired effect in a subject being treated. For instance, in one embodiment, a therapeutically effective amount of a $pO_2$ lowering agent (for example, pyruvate or succinate) is the amount necessary to transiently increase the level of hypoxia (or decrease the $pO_2$) in a tumor cell or tissue in a subject. In another embodiment, a therapeutically effective amount of a $pO_2$ lowering agent (for example, pyruvate or succinate) is the amount necessary to transiently enhance the efficacy of a hypoxia-sensitive agent. In yet another embodiment, a therapeutically effective amount is an amount of a hypoxia-sensitive agent sufficient to result in a biological effect (such as a cytotoxic activity or anti-tumor activity).

In some embodiments, the therapeutically effective amount can be administered as a unitary or singular composition that includes a therapeutically effective combined amount of a hypoxia-sensitive agent, and a $pO_2$ lowering agent that decreases the oxygen partial pressure and that is sufficient to enhance efficacy of the hypoxia-sensitive agent, compared to a control. The amount of the $pO_2$ lowering agent and the hypoxia-sensitive agent together should be effective to treat a target tumor.

TH-302: A 2-nitroimidazole prodrug of the DNA alkylator bromo-isophosphoramide mustard, developed at Threshold Pharmaceuticals, Inc. It is activated only at very low levels of oxygen (hypoxia), which are common in solid tumors (tumor hypoxia). TH-302 is converted selectively to the drug's active form, dibromo isophoramide mustard, a potent DNA alkylator, within hypoxic tumor cells. After conversion to the active form of the drug, the more resistant hypoxic cells are exposed to high concentrations of released cytotoxic agent, which can also diffuse into the surrounding oxygenated regions of the tumor, exerting what is referred to as a bystander effect.

TH-302 exploits the activation of a nitroazole prodrug by a process that involves a one electron reduction mediated by ubiquitous cellular reductases, such as the NADPH cytochrome P450, to generate a radical anion prodrug. In the presence of oxygen (normoxia) the radical anion prodrug reacts rapidly with oxygen to generate the original prodrug and superoxide. Under the low oxygen conditions of the hypoxic zones in tumors, however, the radical anion prodrug undergoes further irreversible reductions to the hydroxylamine followed by elimination, releasing the active drug and an azole derivative.

Tirapazamine (TPZ): Bioreductive drug, 4-hydroxy-1-oxido-1,2,4-benzotriazin-1-ium-3-imine, belonging to the aromatic N-oxide family with selective toxicity for hypoxic cells. Intracellularly, under hypoxic conditions, TPZ undergoes one-electron enzymatic reduction by nicotinamide adenine dinucleotide phosphate cytochrome P450 reductase to yield a transient radical anion that induces the formation of DNA radicals, largely at C4' on the ribose ring, either directly, or through formation of superoxide leading to both single- and double-stranded breaks in DNA, resulting in cytotoxicity.

Transient hypoxia: The temporary decrease in oxygen partial pressure after the administration of an agent, followed by the recovery of the oxygen partial pressure to a level that is equivalent to, or not statistically different from, the level before administration of the agent. Transient hypoxia occurs over the course of hours, rather than days. In certain examples disclosed herein, the transient decrease lasts no more than 20, 16, 15, 10, 6, or 5 hours. The length of time of the transient hypoxia can be extended by sequential doses of a hypoxia-inducing agent. Transient hypoxia can be a temporary decrease in the partial pressure of oxygen from normal levels, or a temporary further decrease in the partial pressure of oxygen which is already below normal levels (for example, in a hypoxic tumor).

Tumor hypoxia: Tumor cell deprivation of an oxygen supply adequate to meet its oxygen demand at a cellular level. As a tumor grows, it often outgrows its blood supply, leaving portions of the tumor (for example, areas of higher cell density) where the oxygen concentration is significantly lower than in healthy or normal tissues. Hypoxic tumors are usually resistant to radiotherapy and chemotherapy but they can be made more susceptible to treatment by increasing the amount of oxygen in them. Alternatively, hypoxic cytotoxins (hypoxia-sensitive therapeutics) can selectively kill the oxygen-deficient tumor cells because they are specifically active at levels of hypoxia that are common in tumors but that are rare in normal tissues. Tumor hypoxia has been demonstrated to be associated with a worse prognosis, making it a determinant of cancer progression and therapeutic response.

Vascular-disruptive agent: An agent that disrupts the formation of blood vessels. An example of a vascular-disruptive agent includes combretastatin-A4-phosphate (CA4P).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein is a method for enhancing the efficacy of a hypoxia-sensitive agent in a subject, comprising administering to a subject a therapeutically effective amount of the hypoxia-sensitive agent and a therapeutically effective amount of a $pO_2$ lowering agent, wherein the amount of $pO_2$ lowering agent administered is sufficient to transiently enhance the hypoxia of the tumor, thereby enhancing the efficacy of the hypoxia-sensitive agent, compared to a control. Particular, non-limiting examples of the $pO_2$ lowering agent include mitochondrial substrates, such as pyruvate or succinate, or analogs thereof (for example, pyruvate-ester), that increase cellular consumption of oxygen and lower $pO_2$ in a subject, or in a tumor cell or targeted portions of it.

In some embodiments, the subject has a tumor. The tumor can be, inter alia, a fibrosarcoma, myxosarcoma, liposarcoma, chondrosarcoma, osteogenic sarcoma, synovioma, mesothelioma, Ewing's tumor, leiomyosarcoma, rhabdomyosarcoma, colon carcinoma, lymphoid malignancy, pancreatic cancer, breast cancer, lung cancer, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, or a central nervous system (CNS) tumor.

In some embodiments of the method, the decrease in oxygen partial pressure is at least a 1%, at least a 2%, at least a 5%, at least a 7.5%, at least a 10%, at least a 15%, at least a 20%, at least a 25%, at least a 30%, at least a 40%, at least a 50%, at least 75% or more decrease from the partial pressure of oxygen prior to administration of the $pO_2$ lowering agent. In other embodiments, the decrease in oxygen partial pressure increases the activity of the hypoxia-sensitive agent, compared to a control. The increase in activity of the hypoxia-sensitive agent can be at least a 1%, at least a 2%, at least a 5%, at least a 7.5%, at least a 10%, at least a 15%, at least a 20%, at least a 25%, at least a 30%, at least a 40%, at least a 50%, or more increase.

In some embodiments of the method, the hypoxia-sensitive agent is a chemotherapeutic agent. The chemotherapeutic agent can be a hypoxia-activated prodrug or a hypoxia-activated drug. Hypoxia-activated prodrugs can be of the 2-nitroimidazole, porphyrin, aromatic di-N-oxide, dinitrobenzamidine, or quinone class. Specific, non-limiting examples of the hypoxia-activated prodrug is banoxantrone (AQ4N; NSC 673504), benzamidine (PR-104; 2-((2-bromoethyl)(2,4-dinitro-6-(2-(phosphonooxy)ethyl)carbamoyl)phenyl)amino) ethyl methanesulfonate), tirapazamine (SR4223), or TH-302. An example of a hypoxia-activated drug is mitomycin C or 3-bromopyruvate.

In particular embodiments of the method, the $pO_2$ lowering agent is administered in a single dose or in multiple doses. In other embodiments of the method, the $pO_2$ lowering agent is administered prior to the hypoxia-sensitive agent or with the hypoxia-sensitive agent.

Also provided herein is a method of treating a subject having a tumor, comprising administering to the subject a therapeutically effective amount of a $pO_2$ lowering agent and therapeutically effective amount of a hypoxia-sensitive agent, thereby treating the subject. Particular, non-limiting examples of the $pO_2$ lowering agent include pyruvate or succinate, and analogs thereof that lower tissue $pO_2$.

It is further provided herein a method of inducing hypoxia in a tumor cell, comprising administering to a subject with a tumor an unlabeled mitochondrial substrate, wherein the amount of the unlabeled mitochondrial substrate is sufficient to transiently induce hypoxia of the tumor cell.

The methods disclosed herein include measuring the partial pressure of oxygen in the tumor after administration of the mitochondrial substrate, and detecting a decrease in the partial pressure of oxygen.

IV. Use of $pO_2$ Lowering Agents to Enhance Hypoxia-Sensitive Agents

Most solid tumors have an abnormal vasculature that allows for poor delivery of oxygen and nutrients to the tumor, creating subpopulations of cells which are either acutely or chronically hypoxic. Hypoxic tumor cells are two to three times more resistant to radiotherapy due to the lack of oxygen required to induce ionizing radiation damage. Hypoxic tumor cells are also less sensitive to most cytotoxic agents (for example, chemotherapeutic agents), in part because of the reduced penetration and delivery of the cytotoxic agents in the tumor tissue and because of the protective effects of hypoxia-regulated genes. Thus, agents that have a higher selective cytotoxicity for hypoxic cells (or increased cytotoxicity under hypoxic conditions), compared to agents that are cytotoxic under normoxic conditions, are useful for targeted chemotherapy against tumors. Moreover, agents that induce hypoxia in tumors can enhance the efficacy of hypoxia-sensitive agents, relative to a control, or enhance the region within a tissue, such as a tumor, that a hypoxia-sensitive agent is active.

It is disclosed herein that the exogenous administration of a $pO_2$ lowering agent, for example, a mitochondrial substrate (such as pyruvate or succinate), to a subject or a tumor surprisingly increases the level of hypoxia (decreases the partial pressure of oxygen) in the tumor, compared to the hypoxia levels in a tumor in the absence of the $pO_2$ lowering agent. It is also disclosed herein that the increased level of hypoxia (decreased oxygen partial pressure) induced by the $pO_2$ lowering agent can increase the activity of a hypoxia-sensitive agent, compared to the activity of the hypoxia-sensitive agent in the absence of the $pO_2$ lowering agent. Thus, increasing the levels of hypoxia (decreasing the oxygen partial pressure) in a subject or in the subject's tumor and/or increasing the activity of a hypoxia-sensitive agent enhances the efficacy of the hypoxia-sensitive agent administered to a tumor or to a subject having a tumor.

It is also disclosed herein that the $pO_2$ lowering effect of the mitochondrial substrate is a transient effect. Thus, the exogenous administration of the $pO_2$ lowering agent results in a temporary decrease in oxygen partial pressure, which is followed by the recovery of the oxygen partial pressure to a level that is equivalent to, or not statistically different from, the level before administration of the agent. The transient effect of the $pO_2$ lowering agents disclosed herein provide an advantage over other hypoxia-inducing agents, for example anti-angiogenic agents (such as sunitinib and bevacizumab), vascular disrupting agents (such as combretastatin-A4-phosphate [CA4P]), echinomycin (hypoxia inducible factor (HIF)-1 inhibitor), and dichloroacetate (PDK1 inhibitor), because the previously known drugs cause long lasting hypoxia (over many days) that can be detrimental to healthy cells and can enhance the malignant properties of tumor cells. Moreover, as the disclosed $pO_2$ lowering agents are naturally found in the cell they are a relatively safe agent. As the $pO_2$ lowering agent-induced hypoxia is transient and reversible, controlled induction of hypoxia (or the controlled decrease in oxygen partial pressure) can be coordinated with administration of a hypoxia-sensitive agent, for example, over specific time periods. In addition, even generalized induction of hypoxia in the subject to achieve tumor hypoxia can be achieved transiently to minimize hypoxic effects on non-tumor tissue. Combination treatment regimens can be developed that involve administering pyruvate and hypoxia-sensitive drugs, followed by conventional radiation therapy or chemotherapy once the hypoxic conditions are sufficiently diminished.

Provided herein are methods of enhancing the efficacy of a hypoxia-sensitive agent in a subject by administering to the subject a therapeutically effective amount of (i) a hypoxia-sensitive agent and (ii) a $pO_2$ lowering agent that is sufficient to enhance efficacy of the hypoxia-sensitive agent. Also provided herein are methods of treating a subject diagnosed with a tumor, comprising administering to the subject a therapeutically effective amount of a $pO_2$ lowering agent and a therapeutically effective amount of a hypoxia-sensitive agent.

In some embodiments, the $pO_2$ lowering agent is a small molecule. Particular, non-limiting examples of a small molecule $pO_2$ lowering agent include pyruvate or succinate (including their salts and analogs thereof). In other embodiments, the $pO_2$ lowering agent is not an anti-angiogenic agent (such as sunitinib and bevacizumab), a vascular disrupting agent (such as combretastatin-A4-phosphate [CA4P]), echinomycin (hypoxia inducible factor (HIF)-1 inhibitor), or dichloroacetate (pyruvate dehydrogenase kinase (PDK)1 inhibitor), or an embolizing agent that physically disrupts blood flow to the tissue. In some embodiments, the administration of a $pO_2$ lowering agent, such as pyruvate or succinate, to a solid tumor (or to a subject having a solid tumor) transiently increases the level of hypoxia (decreases the oxygen partial pressure) in the tumor, compared to the hypoxia levels in a tumor in the absence of the $pO_2$ lowering agent (control levels).

In some embodiments, a hypoxic tumor may be hypoxic in some regions of the tumor, but not hypoxic in other regions, relative to non-tumor tissues or cells. Alternatively, in other embodiments, a hypoxic tumor may be variably hypoxic (exhibit various levels of hypoxia across the tumor tissue). Administration of a $pO_2$ lowering agent (hypoxia-inducer) can induce hypoxia in the tumor such that a larger proportion or percentage of the tumor is transiently hypoxic (i.e., the tumor has a larger hypoxic region or fraction). In one specific non-limiting example, administration of a $pO_2$ lowering agent can render a tumor homogeneously hypoxic. In another embodiment, administration of a $pO_2$ lowering agent can further reduce the $pO_2$ level in any region of a tumor. A $pO_2$ lowering agent can transiently reduce $pO_2$ levels (or transiently increase hypoxia) in normoxic regions in a tumor, in tumor regions that have not reached a threshold hypoxia, or in all regions of a tumor regardless of their endogenous $pO_2$ (hypoxia) levels.

The transient increase in hypoxia levels can be at least a 1%, at least a 2%, at least a 5%, at least a 7.5%, at least a 10%, at least a 15%, at least a 20%, at least a 25%, at least a 30%, at least a 40%, at least a 50%, at least a 75%, or more increase, compared to control hypoxia levels. Similarly, the transient decrease in the oxygen partial pressure can be at least a 1%, at least a 2%, at least a 5%, at least a 7.5%, at least a 10%, at least a 15%, at least a 20%, at least a 25%, at least a 30%, at least a 40%, at least a 50%, at least a 75%, at least an 80%, at least a 90%, or more decrease, compared to oxygen partial pressure levels in a tumor in the absence of the $pO_2$ lowering agent (control levels). One or more $pO_2$ lowering agents that transiently decrease the partial pressure of oxygen can be administered to a tumor or to a subject having a tumor. For example, at least two, at least three, at least four, at least five $pO_2$ lowering agents can be administered, either alone or in combination.

In some embodiments, the administration of a $pO_2$ lowering agent, such as pyruvate or succinate, transiently increases the hypoxic fraction (percent of tissue with $pO_2$<10 mmHg, or percent of pixels in a $pO_2$ image with $pO_2$<10 mmHg) of a tumor, compared to control tumors in the absence of the $pO_2$ lowering agent. The transient increase in hypoxic fraction can be at least a 1%, at least a 2%, at least a 5%, at least a 7.5%, at least a 10%, at least a 15%, at least a 20%, at least a 25%, at least a 30%, at least a 40%, at least a 50%, at least a 76%, at least an 80%, at least a 90%, or more increase, compared to control tumors. In one embodiment, the increase in hypoxic fraction is a transient increase.

In some embodiments, a hypoxia-sensitive agent includes such an agent that localizes in hypoxic tissues. In particular embodiments, the hypoxia-sensitive agent is of the 2-nitroimidazole, porphyrin, aromatic di-N-oxide, dinitrobenzamidine, or quinone class. A hypoxia-sensitive agent can be a chemotherapeutic agent, an anti-proliferative agent, a cytotoxic agent, or a cell killing agent. The hypoxia-sensitive agent can be a hypoxia-activated drug or a hypoxia-activated prodrug. Without being bound by theory, a hypoxia-activated prodrug is converted enzymatically in hypoxic cells (i.e., conditions of low oxygen tension facilitate enzymatic bioactivation) to a stable, persistent cytotoxin. Specific, non-limiting examples of a hypoxia-activated prodrug include banoxantrone (AQ4N; NSC 673504; Novacea Inc.), PR-104 (Proacta Inc.), tirapazamine (SR4223), and TH-302 (Threshold Pharmaceuticals, Inc.). Specific, non-limiting examples of a hypoxia-activated drug include mitomycin C and 3-bromopyruvate.

In some embodiments, the hypoxia-sensitive agent is inactive until exposed to hypoxic conditions of the type found in tumor cells. Hypoxia-sensitive agents administered to a subject are capable of inducing a desired therapeutic effect (for example, a chemotherapeutic effect) when exposed to hypoxic conditions in a subject, for example in a tumor in a subject. In particular embodiments of the method, the transient decrease in oxygen partial pressure in the presence of the $pO_2$ lowering agent (such as a mitochondrial substrate of cellular respiration, such as pyruvate or succinate) increases the activity (for example, the chemotherapeutic, anti-proliferative, cytotoxic, or cell killing activity) of a hypoxia-sensitive agent, compared to the activity of a hypoxia-sensitive agent in the absence of the $pO_2$ lowering agent. The increase in activity of the hypoxia-sensitive agent can be at least about a 1%, at least about a 2%, at least about a 5%, at least about a 7.5%, at least about a 10%, at least about a 15%, at least about a 20%, at least about a 25%, at least about a 30%, at least about a 40%, at least about a 50%, at least about a 75%, at least about an 80%, at least about a 90%, at least about a 100%, at least about a 150%, at least about a 200%, or more increase. In addition, the increase in activity of the hypoxia-sensitive agent can be at least about 10 fold or greater, for example about 20-200 fold or from about 50 to 200 fold. In one embodiment, the increase in activity is a transient increase.

In other embodiments of the method, the transient decrease in oxygen partial pressure in the presence of the $pO_2$ lowering agent (such as a mitochondrial substrate of cellular respiration, such as pyruvate or succinate) enhances or increases the region (surface area or volume) within a tissue, such as a tumor, that is hypoxic (i.e. increases the hypoxic region or fraction) and therefore increases the region that a hypoxia-sensitive agent is active within the tissue. The increase in the region can be at least about a 1%, at least about a 2%, at least about a 5%, at least about a 7.5%, at least about a 10%, at least about a 15%, at least about a 20%, at least about a 25%, at least about a 30%, at least about a 40%, at least about a 50%, at least about a 75%, at least about an 80%, at least about a 90%, at least about a 100%, at least about a 150%, at least about a 200%, or more increase. In one embodiment, the increase in the region is a transient increase. One or more hypoxia-sensitive agents can be administered to a tumor (for example, by regioselective intravascular injection) or systemically to a subject having a tumor. For example, at least two, at least three, at least four, at least five hypoxia-sensitive agents can be administered, either alone or in combination.

A substrate of mitochondrial respiration that increases cellular consumption of oxygen is a molecule upon which an enzyme of cellular respiration acts in the mitochondria. The substrates are primarily the substrates of the citric acid cycle, which are known to include oxaloacetate, citrate, cis-aconitate, isocitrate, oxalosuccinate, alpha-ketoglutarate, succinyl-CoA, succinate, fumarate and malate (L-malate). Under normal oxygen tensions, glucose is catabolized into pyruvate via the glycolysis pathway. Pyruvate then enters the mitochondria and is further catabolized in the tricarboxylic acid (TCA) cycle. Energy in the form of ATP is produced as electrons are transferred through the electron transport chain, which terminates with the donation of electrons to oxygen, thereby converting oxygen into water (consumption of oxygen).

Under conditions of hypoxia, pyruvate catabolism is redirected towards lactic acid (lactate) production and there is a concomitant decrease in mitochondrial respiration and oxygen consumption that increases the $pO_2$ of the cell. The adaptation of cells to hypoxic conditions is an active process, resulting in changes in cellular gene expression initiated by the hypoxia-inducible factor-1 (HIF-1) transcription factor. HIF-1 has been shown to actively regulate the oxygen demand of hypoxic tissues by reducing the activity of the mitochondria and actively suppressing mitochondrial pyruvate catabolism and respiration. More specifically, under hypoxic conditions HIF-1 induces pyruvate dehydrogenase kinase 1 (PDK1), which phosphorylates and inhibits pyruvate dehydrogenase (PDH), thereby limiting the conversion of pyruvate to acetyl-CoA at the entry of the TCA cycle and increasing conversion of pyruvate to lactate. This, in turn, leads to decreased mitochondrial oxygen consumption (i.e., increased oxygenation) in the cells.

It is surprisingly demonstrated herein that the exogenous administration of a $pO_2$ lowering agent, for example, a mitochondrial substrate (such as pyruvate or succinate), to a subject having a hypoxic tumor increases the level of hypoxia (decreases the partial pressure of oxygen), rather than decreases the level of hypoxia, in the tumor by increasing mitochondrial aerobic respiration. Thus, in particular embodiments of the methods disclosed herein, oxygen consumption in a cell or tissue (for example, a tumor) can be increased and hypoxia is increased when the hypoxic cells or tissue are exposed to an exogenous mitochondrial substrate, or a source of the substrate, such as pyruvate or succinate (a $pO_2$ lowering agent), compared to a cell or tumor not exposed to the mitochondrial substrate.

Without being bound by theory, in one specific, non-limiting example, a temporal increase in lactate levels in a tumor or tumor cell is detected when the cells or tumor are exposed to pyruvate, compared to a cell or tumor in the absence of exogenous pyruvate such that, in contrast to normal tissues, a large percentage of administered pyruvate may be initially converted to lactate, while only a small percentage of the pyruvate enters the mitochondria. With a gradual decrease in intracellular pyruvate levels, lactate is converted into pyruvate. The pyruvate is catabolized in the mitochondria, resulting in increased oxygen consumption, compared to a cell or tumor not administered the exogenous pyruvate.

In one embodiment of the method, partial pressure of oxygen levels are measured after the administration of the mitochondrial substrate. In another embodiment, lactate levels are measured after the administration of the mitochondrial substrate. In a further embodiment, partial pressure of oxygen levels and lactate levels are measured after the administration of the mitochondrial substrate. In one specific, non-limiting example, a decrease in the $pO_2$ is detected in the tumor or tumor cell, compared to a cell or tumor not adminstered the mitochondrial substrate. In another specific, non-limiting example, an increase, and then a decrease in the level of lactate is detected. In yet another specific, non-limiting example, a transient increase in the level of lactate and a decrease in the $pO_2$ is detected in the tumor or tumor cell, compared to a cell or tumor not administered the mitochondrial substrate.

In some embodiments, the $pO_2$ lowering agent is not labeled. In other embodiments, a detectable moiety can be linked to the $pO_2$ lowering agent or to the hypoxia-sensitive agent. Detectable moieties suitable for such use include any composition detectable by spectroscopic, photochemical, biochemical, immunochemical, electrical, optical or chemical means. The detectable moieties contemplated for the present disclosure can include, but are not limited to, a fluorescent moiety (e.g., fluorescein, rhodamine, Texas red, and the like), a radioactive moiety (e.g., $^{3}H$, $^{32}P$, $^{125}I$, $^{35}S$) a stable isotope ($^{13}C$); an enzyme moiety (e.g., horseradish peroxidase, alkaline phosphatase), a colorimetric moiety (e.g., colloidal gold, biotin, colored glass or plastic, and the like).

Means of detecting such moieties are well known to those of skill in the art. Thus, for example, radiolabels may be detected using photographic film or scintillation counters, fluorescent markers may be detected using a photodetector to detect emitted illumination, and stable isotopes may be detected using magnetic resonance imaging. Enzymatic labels are typically detected by providing the enzyme with a substrate and detecting the reaction product produced by the action of the enzyme on the substrate, and colorimetric labels are detected by simply visualizing the colored label.

A $pO_2$ lowering agent can be administered in combination with any hypoxia-sensitive agent for the treatment of any tumor. Tumors or neoplasms include new growths of tissue in which the multiplication of cells is uncontrolled and progressive (i.e. hyperproliferation). Some such growths are benign, but others are termed "malignant," leading to death of the organism. Malignant neoplasms or "cancers" are distinguished from benign growths in that, in addition to exhibiting aggressive cellular proliferation, they invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Tumors treatable by the disclosed methods include benign tumors or malignant tumors. Benign tumors and malignant tumors (also referred to as cancer) include solid tumors. Examples of solid tumors include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and central nervous system (CNS) tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma). Thus, selecting a subject in need of treatment with the hypoxia-sensitive agent includes selecting a subject diagnosed with any tumor disclosed herein.

Some embodiments of the presently disclosed methods provide for treatment of a tumor known or suspected of preceding progression to neoplasia or cancer, for example where non-neoplastic cell growth consisting of hyperplasia, metaplasia, or dysplasia has occurred (for review of such abnormal growth conditions, see Robbins and Angell, 1976, Basic Pathology, 2d Ed., W.B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

In certain embodiments, the presently disclosed methods are directed to a method for treating a subject having a tumor. In some embodiments, the disclosed methods are directed to a method of inhibiting cancer or tumor growth, including processes of cellular proliferation, invasiveness, and metastasis in biological systems. Preferably, the method is employed to inhibit or reduce cancer or tumor cell proliferation, invasiveness, metastasis, recurrence, or tumor incidence in living animals, such as mammals (e.g. humans).

Also provided herein is a method of inducing cytotoxicity (cell killing) in cancer or tumor cells or reducing the viability of cancer or tumor cells. For example, the method can be used to induce cytotoxicity in cells of carcinomas, for example carcinomas of the prostate, breast, ovary, testis, lung, colon, or breast.

The disclosed methods can be used for the killing of cancer or tumor cells with less (reduced) cytotoxicity to normal (non-tumor) cells or tissues than is found with conventional cytotoxic therapeutics, preferably without substantial cytotoxicity to the normal cells or tissues. For example, the combination therapy identified herein (a $pO_2$ lowering agent and a hypoxia-sensitive agent) can generate an environment in a tumor or tumor cell that is susceptible to inducing cytotoxicity while producing little or substantially no cytotoxicity in normal (normoxic; non-tumor) cells. Thus, unlike conventional cytotoxic anticancer therapeutics, which typically kill all growing cells, the combination therapy can produce differential cytotoxicity: inducing hypoxia in tumors (or tumor cells), wherein the hypoxic tumors are selectively killed whereas normal (normoxic) cells are spared. Thus, in another embodiment, there is disclosed a method for inducing differential cytotoxicity in cancer cells relative to normal cells or tissue.

The $pO_2$ lowering agent can be administered prior to administering the hypoxia-sensitive agent, combined with the administration of the hypoxia-sensitive agent, following the administration of the hypoxia-sensitive agent, or any combination thereof. Combination treatment of the $pO_2$ lowering agent and the hypoxia-sensitive agent can be achieved either by concurrent administration of the agents together, or sequential administration in sufficient close temporal proximity for the $pO_2$ lowering agent to increase the level of hypoxia in the tumor, increase the proportion (or percentage) of the tumor that is hypoxic (increase the hypoxic region or fraction of the tumor), or increase the activity of the hypoxia-sensitive agent.

Sequential administration of the $pO_2$ lowering agent and the hypoxia-sensitive agent, for example, can include the administration of the $pO_2$ lowering agent and the hypoxia-sensitive agent no more than 30 seconds, no more than 1 minute, no more than 2 minutes, no more than 3 minutes, no more than 4 minutes, no more than 5 minutes, no more than 10 minutes, no more than 20 minutes, no more than 30 minutes, no more than 40 minutes, no more than 50 minutes, no more than 60 minutes, no more than 90 minutes, no more than 2 hours, no more than 3 hours, no more than 4 hours, or no more than 5 hours apart. The $pO_2$ lowering agent can be administered first, followed by the hypoxia-sensitive agent, or vice-versa. In some embodiments, the $pO_2$ lowering agent and the hypoxia-sensitive agent are repeatedly administered, for example alternately administered.

In one embodiment, the $pO_2$ lowering agent is administered in one dose. For example, the $pO_2$ lowering agent is administered prior to, in combination with, or following the first dose of a hypoxia-sensitive agent. In other embodiments, the $pO_2$ lowering agent is administered in two or more doses (for example, at least 2, at least 3, at least 4, at least 5, or more doses), such as prior to each dose of a hypoxia-sensitive agent. The $pO_2$ lowering agent can further be administered after one or more doses of a hypoxia-sensitive agent. The doses can be administered on the same day or at regular intervals over the course of hours, days, weeks, months, or years.

In yet other embodiments, the $pO_2$ lowering agent is administered in repeated sequential doses (for example, at least 2, at least 3, at least 4, at least 5, or more sequential doses) in order to sustain the increased level of hypoxia (decreased oxygen partial pressure) in the tumor, the increased proportion of hypoxic tumor tissue, and/or the increased activity of the hypoxia-sensitive agent until, for example, the concentration of the hypoxia-sensitive agent decreases below therapeutically effective levels at the site of the tumor. In a particular non-limiting example, the $pO_2$ lowering agent is administered in two or more doses (for example, at least 2, at least 3, at least 4, at least 5, or more doses), wherein the first dose of the $pO_2$ lowering agent is administered prior to a single dose of a hypoxia-sensitive agent, and one or more subsequent doses of the $pO_2$ lowering agent are administered following the single dose of the hypoxia-sensitive agent in order to sustain the increased level of hypoxia (decreased oxygen partial pressure) in the tumor (or to sustain the increased hypoxic fraction and/or the increased activity of the hypoxia-sensitive agent) until, for example, the concentration of the hypoxia-sensitive agent decreases below therapeutically effective levels at the site of the tumor. In some embodiments, the sequential, repeated administrations of the $pO_2$ lowering agent can be about every 30 minutes, about every 1 hour, about every 2 hours, about every 3 hours, about every 4 hours, about every 5 hours, or more. The number of sequential administrations and timing between sequential administrations of the $pO_2$ lowering agent will depend upon, among other factors, the half-life of the hypoxia-sensitive agent.

In other particular non-limiting examples, a single or sequential administration of the $pO_2$ lowering agent is combined with a prolonged (for example, at least about 4 hours, at least about 5 hours, at least about 6 hours, at least about 7 hours, at least about 8 hours, at least about 9 hours, at least about 10 hours, at least about 12 hours, at least about 15 hours, at least about 20 hours, at least about 24 hours, at least about 36 hours, or more) single administration of a hypoxia-sensitive agent, or multiple administrations (for example, at least 2, at least 3, at least 4, at least 5, at least 10 or more doses) of a hypoxia-sensitive agent.

In some embodiments, the $pO_2$ lowering agent and hypoxia-sensitive agent can be administered as a unitary or singular composition that includes a therapeutically effective combined amount of a hypoxia-sensitive agent, and a $pO_2$ lowering agent that decreases the oxygen partial pressure and that is sufficient to enhance efficacy of the hypoxia-sensitive agent, compared to a control. The amount of the $pO_2$ lowering agent and the hypoxia-sensitive agent together should be effective to treat a target tumor. In further embodiments, a therapeutically effective amount of a hypoxia-sensitive agent and a therapeutically effective amount of a $pO_2$ lowering agent are administered.

It is contemplated that further agents can be administered, in addition to the $pO_2$ lowering agent and the hypoxia-sensitive agent disclosed herein. In some embodiments, radiotherapy, chemotherapeutic agents, or other anti-tumor agents (such as anti-angiogenic or vascular disruptive agents) that are not activated under hypoxic conditions (or which are inactive or less active under hypoxic conditions) can be administered to the tumor, or to the subject having the tumor, following the completion of the transient effect of the $pO_2$ lowering agent. Examples of chemotherapeutic agents include melphalan (Alkeran™), cyclophosphamide (Cytoxan™), cisplatin (Platinol™), busulfan (Busilvex™, Myleran™), doxorubicin (adriamycin), and paclitaxel. Examples of anti-angiogenic agents include sunitinib, sorafenib, and bevacizumab. Anti-angiogensis agents also include native angiogenesis inhibitors, for example angiostatin and endostatin. Examples of a vascular disrupting agent include combretastatin-A4-phosphate (CA4P) and taxanes.

Radiotherapy, chemotherapeutic agents, or anti-tumor agents can be administered after the oxygen partial pressure in the tumor recovers to the level prior to the administration of the $pO_2$ lowering agent. In specific, non-limiting examples, the radiotherapy or chemotherapeutic agent can be administered at least about 30 minutes, at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 12 hours, at least about 18 hours, at least about 24 hours after the administration of the $pO_2$ lowering agent. In other specific, non-limiting examples, the radiotherapy or chemotherapeutic agent can be administered at least about 10 minutes, at least about 15 minutes, at least about 20 minutes, at least about 30 minutes, at least about 40 minutes, at least about 50 minutes, at least about 60 minutes, at least about 90 minutes, at least about 2 hours, at least about 3 hours, at least about 4 hours, at least about 5 hours, at least about 6 hours, at least about 7 hours, at least about 8 hours, at least about 9 hours, at least about 10 hours, at least about 12 hours, at least about 18 hours, at least about 24 hours after the oxygen partial pressure in the tumor recovers to the level prior to the administration of the $pO_2$ lowering agent.

Oxygen partial pressure levels in tissues (for examples tumors) can be measured by any means known to one of skill in the art. In one embodiment, measurement of tumor oxygenation uses fiber-optic sensors, such as those of the Oxylite system (Oxford Optronix, Oxford, United Kingdom), which is based on probe-based measurements of oxygen-dependent fluorescence quenching and signal detection over fiber-optic cables. The system employs concurrent measurements of tissue temperature using thermocouples. In one specific, non-limiting example of the method, two oxygen probes are inserted into different parts of the tumor: one close to the surface, the other at the center of the tumor. A third probe is inserted into the muscle of the opposite hind leg, as a control. Thermocouples are inserted into the tumor and the muscle. Oxygen and temperature values are monitored constantly throughout the experiment. In other embodiments, $pO_2$ levels can be measured using magnetic resonance imaging (MRI) or oxygen-sensitive needle electrodes.

Tumor oxygen status can be investigated, or screened, using the EPR imaging (EPRI) technique. EPR is a spectroscopic technique similar to NMR but it detects paramagnetic species which have unpaired electrons. As the line width of paramagnetic species varies depending on oxygen concentration, EPR combined with an appropriate paramagnetic tracer (for example, triarylmethyl radicals (TAM)) can be used for estimating tissue oxygen status. In one embodiment, EPRI can be used to determine whether a tumor is sufficiently hypoxic (either by measuring tumor $pO_2$ or the hypoxic fraction of the tumor) such that administration of pyruvate prior to the administration of a hypoxia-sensitive agent may not be necessary. In another embodiment, EPRI can be used to determine the hypoxic status of different tumors (for example, tumors of different type or stage) following pyruvate administration to determine if the tumors respond to pyruvate treatment similarly. EPRI can therefore be used to determine whether dosage or timing of pyruvate administration prior to administration of a hypoxia-sensitive agent should be varied depending upon the tumor type or stage.

Tumor hypoxia can also be detected using hypoxia-binding chemical markers. These markers are nitroheterocyclic compounds which exhibit a particular metabolism under hypoxic cellular conditions, and hence can covalently bind to intracellular macromolecules (e.g. proteins, RNA, lipids and DNA). These reduced moieties trapped into hypoxic cells, can be detected by immunofluorescence on tissue section or by flow cytometry using specific antibodies. Tagged with an appropriate radioactive isotope, these reduced moieties could also be detected by nuclear medicine techniques. Misonidazole is the prototype of hypoxia-binding chemical markers. In addition, tri- and pentafluorinated nitroimidazole derivates, designated EF3 and EF5, respectively, have been synthesized (U.S. Pat. No. 5,540,908 in name of Koch).

In another embodiment, $pO_2$ levels can be measured by histology by comparing the pimonidazole hypoxic fraction with total vital tissue. Pimonidazole is a well-established immunohistochemical marker of tumor hypoxia. In particular examples of the method, tumors are cryosectioned and sections fixed and stained with fluorescently-labeled antibodies. Slides are scanned using a fluorescence microscope equipped with a computerized stage and shutter. After fluorescence imaging, the same sections are stained with hematoxylin/eosin to determine vital tumor areas. The measurement of $pO_2$ level is the differences in the pimonidazole-positive vs. overall vital tumor area.

V. Administration of Agents

As used herein, an effective amount of a $pO_2$ lowering agent is an amount sufficient to result in a biological effect (such as increasing the hypoxia level in a tumor cell, decreasing the oxygen partial pressure in a tumor cell, and/or increasing the activity of a hypoxia-sensitive agent). In one embodiment, an effective amount of a $pO_2$ lowering agent is therapeutically effective amount. A therapeutically effective amount is an amount sufficient to result in a biological effect (such as increasing the hypoxia level in a tumor or in a subject having a tumor, decreasing the oxygen partial pressure in a tumor or in a subject having a tumor, and/or increasing the activity of a hypoxia-sensitive agent). One skilled in the art can readily determine a therapeutically effective amount of a $pO_2$ lowering agent to be administered to a given subject, by taking into account factors such as the size and weight of the subject; the extent of disease progression; the age, health and sex of the subject; the route of administration; and whether the administration is regional or systemic. In other embodiments, a therapeutically effective amount is an amount of a hypoxia-sensitive agent sufficient to result in a biological effect (such as a cytotoxic activity or anti-tumor activity).

For example, a therapeutically effective systemic amount of a $pO_2$ lowering agent or a hypoxia-sensitive agent can be based on the approximate body weight of a subject to be treated. For more targeted delivery of the agent, for example by targeted delivery to the site of a tumor by intravascular infusion into an artery that selectively perfuses a tumor or an organ in which it is contained, dosages can be determined empirically or by tumor volume and/or location. Such effective amounts can be exogenously administered by any suitable route, such as, for example, parenterally or enterally. In one specific, non-limiting example, the effective amount of the administered $pO_2$ lowering agent is an isotonic concentration. In another non-limiting example, a therapeutically effective amount of the $pO_2$ lowering agent is administered as a bolus amount (e.g., administered to raise its concentration in blood to an effective level). In a further non-limiting example, a therapeutically effective amount of the $pO_2$ lowering agent is at least 0.50 mmol/kg body weight. In other non-limiting examples, a therapeutically effective amount of the $pO_2$ lowering agent is at least about 0.05 mmol/kg, at least about 0.06 mmol/kg, at least about 0.07 mmol/kg, at least about 0.08 mmol/kg, at least about 0.09 mmol/kg, at least about 0.1 mmol/kg, at least about 0.2 mmol/kg, at least about 0.3 mmol/kg, at least about 0.5 mmol/kg, at least about 1.0 mmol/kg, at least about 1.05 mmol/kg, at least about 1.1 mmol/kg, at least about 1.15 mmol/kg, at least about 1.2 mmol/kg, at least about 1.25 mmol/kg, at least about 1.30 mmol/kg, at least about 1.35 mmol/kg, at least about 1.40 mmol/kg, at least about 1.45 mmol/kg, at least about 1.5 mmol/kg, at least about 1.75 mmol/kg, at least about 2.0 mmol/kg, at least about 5.0 mmol/kg, or more. Further non-limiting ranges for a therapeutically effective amount of the $pO_2$ lowering agent are about 0.05 mmol/kg to about 1.5 mmol/kg, about 0.07 mmol/kg to about 1.3 mmol/kg, about 0.1 mmol/kg to about 1.1 mmol/kg, about 0.12 mmol/kg to about 1.0 mmol/kg, about 0.15 mmol/kg to about 0.70 mmol/kg, or about 0.20 mmol/kg to about 0.50 mmol/kg.

Other non-limiting therapeutically effective amounts of an agent (for example, a hypoxia-sensitive agent) within the methods and formulations of the disclosure are at least about 0.01 mg/kg, at least about 0.02 mg/kg, at least about 0.03 mg/kg, at least about 0.04 mg/kg, at least about 0.05 mg/kg, at least about 0.06 mg/kg, at least about 0.07 mg/kg, at least about 0.08 mg/kg, at least about 0.09 mg/kg, at least about 0.10 mg/kg, at least about 0.20 mg/kg, at least about 0.30 mg/kg, at least about 0.40 mg/kg, at least about 0.50 mg/kg, at least about 0.60 mg/kg, at least about 0.70 mg/kg, at least about 0.80 mg/kg, at least about 0.90 mg/kg, at least about 1.0 mg/kg, at least about 2.0 mg/kg, at least about 5.0 mg/kg, at least about 7.0 mg/kg, at least about 10 mg/kg, at least about 20 mg/kg, at least about 30 mg/kg, at least about 40 mg/kg, at least about 50 mg/kg, at least about 60 mg/kg, at least about 70 mg/kg, at least about 80 mg/kg, at least about 90 mg/kg, at least about 100 mg/kg, at least about 125 mg/kg, at least about 150 mg/kg, at least about 175 mg/kg, at least about 200 mg/kg, at least about 250 mg/kg, at least about 500 mg/kg, Therapeutically effective ranges of an agent are about 0.01 mg/kg body weight to about 20 mg/kg body weight, such as about 0.05 mg/kg to about 5 mg/kg body weight, about 0.2 mg/kg to about 2 mg/kg body weight, about 0.1 mg/kg to about 0.5 mg/kg body weight, or about 0.1 mg/kg to about 200 mg/kg body weight.

One skilled in the art can also readily determine an appropriate dosage regimen for the exogenous administration of a $pO_2$ lowering agent or a hypoxia-sensitive agent disclosed herein to a given subject. For example, a $pO_2$ lowering agent or a hypoxia-sensitive agent can be administered to the subject once (e.g., as a single injection or deposition). Alternatively, a $pO_2$ lowering agent and/or a hypoxia-sensitive agent can be administered once, twice, or more daily to a subject for a period of from about three to about twenty-eight days, more particularly from about seven to about ten days. In particular dosage regimens, a $pO_2$ lowering agent and/or a hypoxia-sensitive agent is administered once a day for seven days, once a week for several weeks, once a month for several months.

Therapeutic agents can be administered to a subject in need of treatment using any suitable means known in the art. $pO_2$ lowering agents and/or hypoxia-sensitive agents are preferably administered to a subject in a pharmaceutically acceptable carrier or diluent. The choice of pharmaceutically acceptable carrier will depend on a variety of factors, including the type of inhibitor, route of administration, and the disease to be treated. To formulate the pharmaceutical compositions, the agents can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), and solubility enhancing agents (for example, cyclodextrins and derivatives thereof), stabilizers (for example, serum albumin) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. In particular embodiments, the $pO_2$ lowering agents disclosed herein may be administered as a free form (for example, as pyruvic acid or succinic acid) or as a salt, and in some embodiments it is the sole pharmacological moiety, i.e. it is not part of a larger molecule, such as calcium pyruvate or doxylamine succinate, that has a pharmacological activity other than as a hypoxia inducing agent.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7. In particular embodiments, the $pO_2$ lowering agents disclosed herein (for example, pyruvate or succinate) may be administered in an isotonic solution.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the agents can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

The compositions disclosed herein (one or both of the hypoxia-sensitive agent and the $pO_2$ lowering agent) can be administered directly to a tumor (for example, by intratumoral injection) or regionally (for example, to the blood vessels supplying the tumor or the tissue in which the tumor is contained). However, in other embodiments, one or both are administered systemically (for example, intravascularly).

Administration can be accomplished by single or multiple doses. The dose required will vary from subject to subject depending on the species, age, weight and general condition of the subject, the particular type of $pO_2$ lowering agent and/or hypoxia-sensitive agent being used and the mode of administration. An appropriate dose can be determined by one of ordinary skill in the art using only routine experimentation. If administered in multiple doses, the time between delivery of each dose can vary between hours, days, weeks, months and years.

The administration of the agents can be for either prophylactic or therapeutic purposes. When provided prophylactically, the agents are provided in advance of any symptom. The prophylactic administration of the agents serves to prevent or ameliorate any subsequent disease process. When provided therapeutically, the compound is provided at (or shortly after) the onset of a symptom of disease.

The following examples are provided to illustrate certain particular features and/or embodiments. These examples should not be construed to limit the disclosure to the particular features or embodiments described.

EXAMPLES

Example 1

Transient Decrease in Tumor Oxygenation after Intravenous Administration of Pyruvate This example shows that tumor $pO_2$ transiently decreases after pyruvate injection.

Hyperpolarization of $^{13}C$-labeled compounds was found to greatly increase the magnetic resonance (MR) signal by more than 10000-fold (Ardenkjær-Larsen et al., *Proc Natl Acad Sci USA,* 100:10158-10163, 2003), and provides sufficient signals to image the hyperpolarized compounds and their metabolites in vivo. This technique provides the ability to monitor metabolic processes of the hyperpolarized substrates in live animals (Golman et al., *Proc Natl Acad Sci USA,* 103:11270-11275, 2006; and Gallagher et al., *Prog Nucl Mag Res Sp,* 55:285-295, 2009). The use of $^{13}C$-labeled pyruvate for cancer studies is of great interest, since pyruvate is involved in important bioenergetic processes that are altered in pathologic conditions such as cancer.

Acetyl-CoA and $CO_2$ are formed from pyruvate in the reaction catalyzed by pyruvate dehydrogenase under aerobic conditions; subsequently acetyl-CoA enters the tricarboxylic acid (TCA) cycle. Under hypoxic conditions, pyruvate is metabolized to lactate in the reaction catalyzed by lactate dehydrogenase (LDH). As tumors grow, they become hypoxic since the new blood vessels are aberrant and unable to deliver oxygen, nutrients or drugs efficiently (Brown et al., *Cancer Res,* 58:1408-1416, 1998; and Matsumoto et al., *Proc Natl Acad Sci USA,* 106:17898-17903, 2009). Therefore, anaerobic metabolism of pyruvate to lactate is increased in tumors. The formation of lactate from pyruvate is also increased in some kinds of tumors even in the presence of adequate levels of oxygen through aerobic glycolysis also known as the Warburg effect (Board et al., *Biochem J,* 265: 503-509, 1990; and Warburg et al., *Int J Radiat Oncol Biol Phys,* 14:831-838, 1988). Studies using hyperpolarized [1-$^{13}$C]pyruvate showed significantly higher level of [1-$^{13}$C] lactate in tumors compared with normal tissue, and the formation of lactate was decreased by chemotherapies (Golman et al., *Cancer Res,* 66:10855-10860, 2006; and Day et al., *Nat Med,* 13:1382-1387, 2007). These studies suggest that lactate is the main metabolite of pyruvate in tumors, and the [1-$^{13}$C] lactate to [1-$^{13}$C]pyruvate ratio can be a useful marker for estimating tumor progression and response to therapy.

Although anaerobic metabolism of pyruvate is dominant in tumors, a part of pyruvate is still aerobically metabolized. Injection of hyperpolarized [1-$^{13}$C]pyruvate for MR spectroscopic imaging into tumor-bearing animals at the required doses is believed to induce consumption of more cellular oxygen via mitochondrial oxidative phosphorylation. Since oxygen concentration in tumors is a critical factor to determine outcomes of cancer therapies (Gatenby et al., *Int J Radiat Oncol Biol Phys,* 14:831-838, 1988; and Dewhirst, *Radia Res,* 172:653-665, 2009), the temporal profile of tumor oxygen status was investigated using EPR imaging (EPRI) technique after pyruvate administration.

EPR is a spectroscopic technique similar to nuclear magnetic resonance (NMR) but detects paramagnetic species which have unpaired electrons. Since the line width of paramagnetic species varies depending on oxygen concentration, EPR combined with an appropriate paramagnetic tracer is widely used for estimating tissue oxygen status (Goda et al., *Cancer Res,* 55:2249-2252, 1995; and Yasui et al., *Cancer Res,* 70:6427-6436, 2010). Recent development of EPRI with triarylmethyl (TAM) radicals as a tracer make it possible to non-invasively visualize tissue oxygen concentration in live animals. The EPRI technique using TAM as a tracer is capable of monitoring tumor oxygen status as a function of tumor growth and its response to therapy (Matsumoto et al., *Magn Reson Med,* 55:1157-1163, 2006; and Yasui et al., *Cancer Res,* 70:6427-6436, 2010). In this study, changes of partial pressure of oxygen ($pO_2$) in squamous cell carcinoma (SCC) implanted in mouse leg after [1-$^{13}$C]pyruvate administration was examined using EPRI.

Materials and Methods

Animal Studies

All animal experiments were carried out in compliance with the *Guide for the care and use of laboratory animal resources* (National Research Council, 1996) and approved by the National Cancer Institute Animal Care and Use Committee. Female C3H/Hen mice were supplied by the Frederick Cancer Research Center, Animal Production (Frederick, Md.). SCCVII solid tumors were formed by injecting $5\times10^5$ SCC cells subcutaneously into the right hind leg of C3H mice. Body weight measured before the experiments was 21-27 g. In EPRI and MRI measurements, mice were anesthetized by isoflurane (4% for induction and 2% for maintaining anesthesia) in medical air (750 mL/min) and positioned prone with their tumor-bearing legs placed inside the resonator. During the measurements, the breathing rate of the mice was monitored with a pressure transducer (SA Instruments Inc.) and maintained at 60±10 breaths per minute. Core body temperature was also monitored with a non-magnetic rectal temperature probe (FISO) and maintained at 37±1° C. with a flow of warm air. For administration of TAM and [1-$^{13}$C]pyruvate solution, a 30-gauge needle was cannulated into the tail vein and extended using polyethylene tubing (PE-10).

EPR Imaging with Pyruvate Injection

Technical details of the EPR scanner operating at 300 MHz, data acquisition based on the single-point imaging (SPI) modality, image reconstruction, and the oxygen mapping procedure were described previously (Matsumoto et al., *Magn Reson Med,* 55:1157-1163, 2006; and Matsumoto et al., *J Clin Invest,* 118:1965-1973, 2008). Isotonic [1-$^{13}$C] pyruvate solution (pH 7.4) was prepared by dissolving 30 μL of [1-$^{13}$C]pyruvic acid in 4.5 mL of alkaline solution containing 100 mg/L EDTA. After the mouse was placed in the resonator, TAM (OX063, GE Healthcare) was injected intravenously through the cannula placed in the tail vein. TAM was given as a 1.125 mmol/kg bolus followed by 0.04 mmol/kg/min continuous injection. After acquiring the first EPR data set, 1.15 mmol/kg bolus (300 μL of 96 mM) [1-$^{13}$C] pyruvate solution was injected intravenously through the cannula. EPRI measurements were carried out 30 minutes and 1 hour after [1-$^{13}$C]pyruvate injection. Then, the mouse was released. The mouse was anesthetized and canulated again, 1.125 mmol/kg TAM was injected to the mouse, and EPRI measurement was carried out 5 hours after the [1-$^{13}$C]pyruvate injection.

EPR signals were collected following the RF excitation pulses (60 ns, 80 W, 70° flip angle) using an analog digital converter (200 Msamples/s). EPR measurements were started 3 minutes after TAM injection, and it took 9 minutes to obtain a data set for a 3D image. The repetition time (TR) was 6.0 μs. The FIDs (free induction decays) were collected under a nested looping of the x, y, z gradients and each time point in the FID underwent phase modulation enabling 3D spatial encoding. In order to get reproducible values of $T_2$* and to retain a more or less uniform image resolution, a set of 3 gradients was used, and data for corresponding images were collected in an interleaved fashion (Matsumoto et al., *Magn Reson Med,* 55:1157-1163, 2006). If the power spectrum of the pulse is uniform throughout the k-space for all the gradients used, the spatial resolution is simply defined by FOV (field of view) and the number of k-samples (elements in k-space). The spatial resolution was 1.8 mm, although the pixel resolution was digitally enhanced.

Co-Registration of $pO_2$ Images from EPRI with Anatomic Images from MRI

Anatomical images of the tumor-bearing leg were obtained using 7 T MRI after the EPRI measurements. The $pO_2$ images from EPRI and the anatomic images from MRI were co-registered, since EPRI does not give anatomical information. An identical parallel coil resonator (17 mm inner diameter and 25 mm long) with Q switch was used for both EPRI and MRI operating at 300 MHz (Matsumoto et al., *J Clin Invest,* 118:1965-1973, 2008).

MRI scans were conducted using a 7 T scanner controlled with ParaVision 5.0 (Bruker BioSpin MRI GmbH). After a quick assessment of the sample position by a fast low-angle shot (FLASH) tripilot sequence, $T_2$-weighted anatomical images were obtained using a fast spin echo sequence (RARE) with an echo time (TE) of 13 ms, TR of 2.5 s, 14 slices, RARE factor 8, resolution of 0.109×0.109 mm, and acquisition time of 80 s. For convenience of co-registration with EPRI, all MRI images had the same FOV of 2.8 cm and slice thickness of 2 mm. Co-registration of EPRI and MRI images was accomplished using code written in MATLAB (Mathworks) as described previously (Matsumoto et al., *J Clin Invest,* 118:1965-1973, 2008).

X-Irradiation

Mice were fixed in the specially designed jig for X-irradiation, by which mice were restricted from moving without anesthesia. X-irradiation (12 Gy) was delivered to tumor-bearing leg 6 days after SCC tumor implantation using a XRAD-320 (Precision X-ray Inc.).

Immunohistochemical Analysis

A hypoxia marker, pimonidazole, was given to tumor-bearing mice intravenously 30 minutes before excising tumors. The mice were euthanized, and tumor tissues were removed from mice. The tumor tissues were fixed with 4% paraformaldehyde and frozen using ultracold ethanol. The frozen tumors were sectioned to 10 μm thick using a cryostat, and the sections were thaw-mounted on glass slides. After blocking non-specific binding sites with Protein Block Serum-Free reagent (Dako North America Inc., Carpinteria, Calif.), the slides were covered by rabbit anti-pimonidazole antisera (Natural Pharmacia International, Inc., Burlington, Mass.; 1:250) overnight at 4° C. The sections were incubated with Alexa Fluor 555 anti-rabbit secondary antibody (Invitrogen, Carlsbad, Calif.; 1:500). Then they were mounted on Prolong Gold antifade reagent with DAPI (Invitrogen). Fluorescence microscopic observation was performed using an Axiovert 200 inverted fluorescent microscope (Carl Zeiss), and images of tissues were captured using Image-Pro Plus Ver. 4.0 imaging software. The pimonidazole positive area was quantified using Image J software.

Statistical Analysis

All results were expressed as the mean±SEM. The differences in means of groups were determined by 2-tailed Student's t test. The minimum level of significance was set at $P<0.05$.

Results and Discussion

Tumor $pO_2$ Decreases after Administration of [1-$^{13}$C]-Pyruvate

To demonstrate changes in tumor $pO_2$ in response to the intravenous administration of a systemic bolus dose of pyruvate (1.15 mmol/kg body weight; 300 μL of 96 mM), EPRI experiments on a group of mice implanted with SCC tumors were carried out after MRI experiments of hyperpolarized [1-$^{13}$C]pyruvate, namely 1-2 hours after hyperpolarized [1-$^{13}$C]pyruvate injection, and compared with a group of mice with tumors which did not receive pyruvate injection (control group). FIG. 1A and FIG. 1B show the center slices of $T_2$ weighted anatomic images from MRI and the corresponding $pO_2$ maps from EPRI in a SCC tumor leg of a control mouse and a mouse after hyperpolarized [1-$^{13}$C]pyruvate MRI experiments. The results show that the median $pO_2$ value in the control tumor group was 11.7±0.7 mmHg, whereas after [1-$^{13}$C]pyruvate injection, the $pO_2$ value decreased to 9.2±1.1 mmHg (FIG. 1C). The tumors were more hypoxic after hyperpolarized [1-$^{13}$C]pyruvate MRI experiments compared with the control tumors. From the $pO_2$ images of the tumor the hypoxic fraction (pixels with $pO_2<10$ mm Hg) was determined. It was found that the hypoxic fraction after pyruvate administration (58.5±10.2%) was larger than the hypoxic fraction in control tumors (37.1±5.6%) (FIG. 1D). Hence, pyruvate administration results in a decrease of tumor $pO_2$ and a corresponding increase in hypoxic fraction.

Pyruvate Injection Transiently Reduces Tumor $pO_2$

Figure 2A:
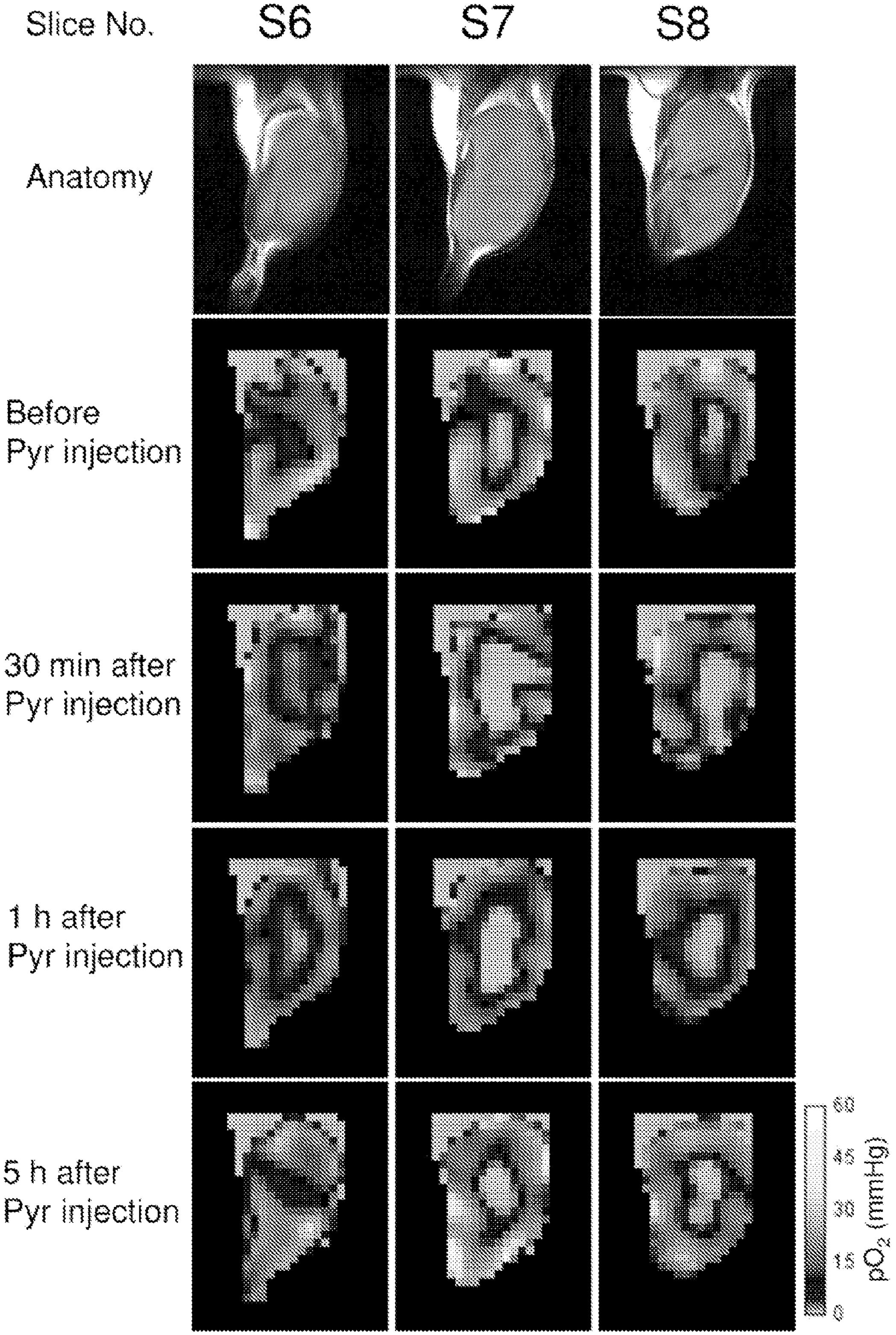
FIGS. 2A-2D are a series of digital images and graphs showing non-invasive monitoring of tumor $pO_2$ by Electron Paramagnetic Resonance (EPR) Imaging (EPRI) and the effects of pyruvate injection.
Figure 2B:
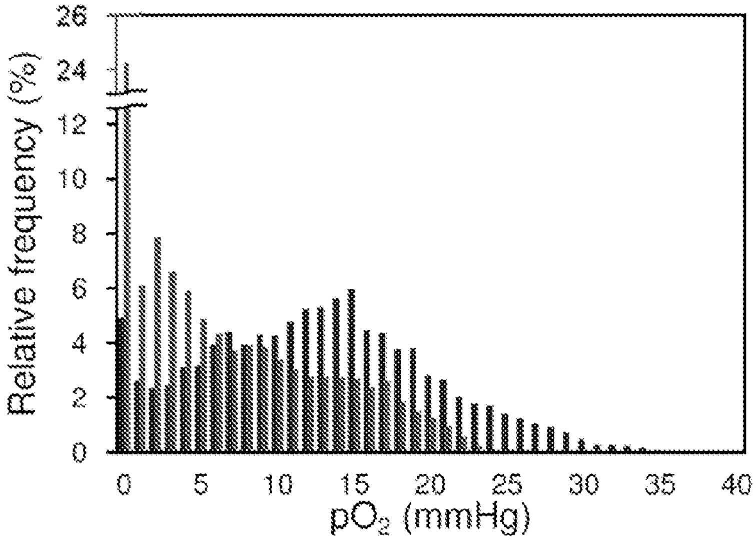
Figure 2C:
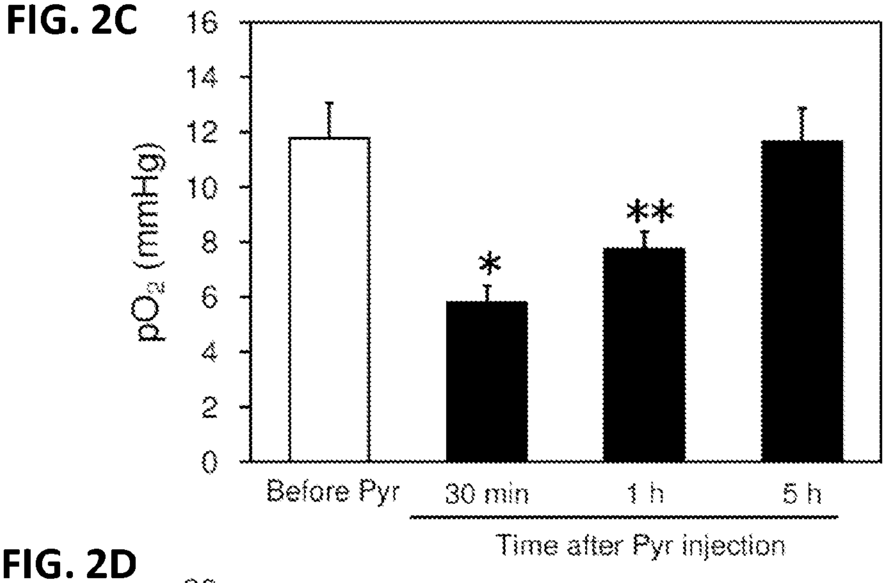
Figure 2D:
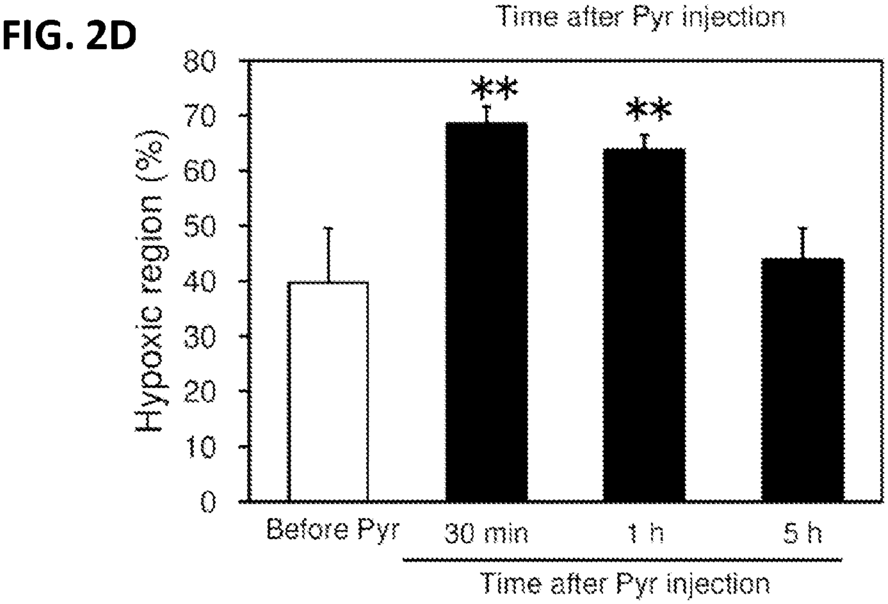

Pyruvate is mainly metabolized to lactate, alanine, and acetyl-CoA+$CO_2$ in tumors. Large MR signal attributed to [1-$^{13}$C]lactate was detected in the SCC tumors immediately after hyperpolarized [1-$^{13}$C]pyruvate injection, but [1-$^{13}$C] alanine and $^{13}$C-bicarbonate which (in equilibrium with $^{13}CO_2$) were at negligible levels. These results suggest that anaerobic lactate formation catalyzed by LDH is a main pathway of pyruvate metabolism in the SCC tumor. However, decreased tumor $pO_2$ level after hyperpolarized [1-$^{13}$C]pyruvate MRI experiments as shown in FIG. 1 indicates that a significant fraction of tumor oxygen is consumed by exogenously injected [1-$^{13}$C]pyruvate probably due to increase of $O_2$-dependent metabolism of pyruvate. To elucidate changes in the oxygen status of the SCC tumor as a function of time following pyruvate administration, sequential $pO_2$ imaging experiments were carried out at different times after pyruvate administration. The pyruvate solution was not hyperpolarized, but labeled compound was used in this experiment. FIG. 2A shows three adjacent slices of anatomic and $pO_2$ images in a SCC tumor leg measured 9 days after tumor implantation. The $pO_2$ imaging experiments were carried out before, 30 minutes, 1 hour, and 5 hours after [1-$^{13}$C]pyruvate injection. In the $pO_2$ maps, a significant decrease in $pO_2$ was observed in the tumor 30 minutes after [1-$^{13}$C]pyruvate injection. The frequency histogram of $pO_2$ in the tumor region 30 minutes after pyruvate injection displayed a leftward shift compared with the histogram before pyruvate injection (FIG. 2B). The $pO_2$ in the tumor was lower even 1 hour after injection, but recovered to the pre-injection level 5 hours after injection (FIG. 2A). Median tumor $pO_2$ value in the SCC tumors was 11.8±1.3 mmHg before pyruvate injection, which decreased to 5.8±0.6 mmHg 30 minutes after injection (FIG. 2C). It gradually recovered to 7.7±0.6 mmHg 1 hour after and 11.6±1.2 mmHg 5 hours after pyruvate injection. There was no significant difference in tumor $pO_2$ between before and 5 hours after pyruvate injection. Hypoxic fraction in the tumors showed a similar tendency as the median $pO_2$ (FIG. 2D). Percentage of hypoxic region in the tumors was significantly larger 30 minutes and 1 hour after pyruvate injection (68.5±3.0% and 63.8±2.6%, respectively) than that before the injection (39.7±9.8%), and recovered to pre-injection level 5 hours after the injection (43.9±5.7%). Such trends of decrease in tumor oxygenation were observed even when the dose of pyruvate was half. The tumor $pO_2$ decreased by 32% 30 minutes after the half dose of [1-$^{13}$C]pyruvate (0.58 mmol/kg b. w.) injection.

Figure 3A:
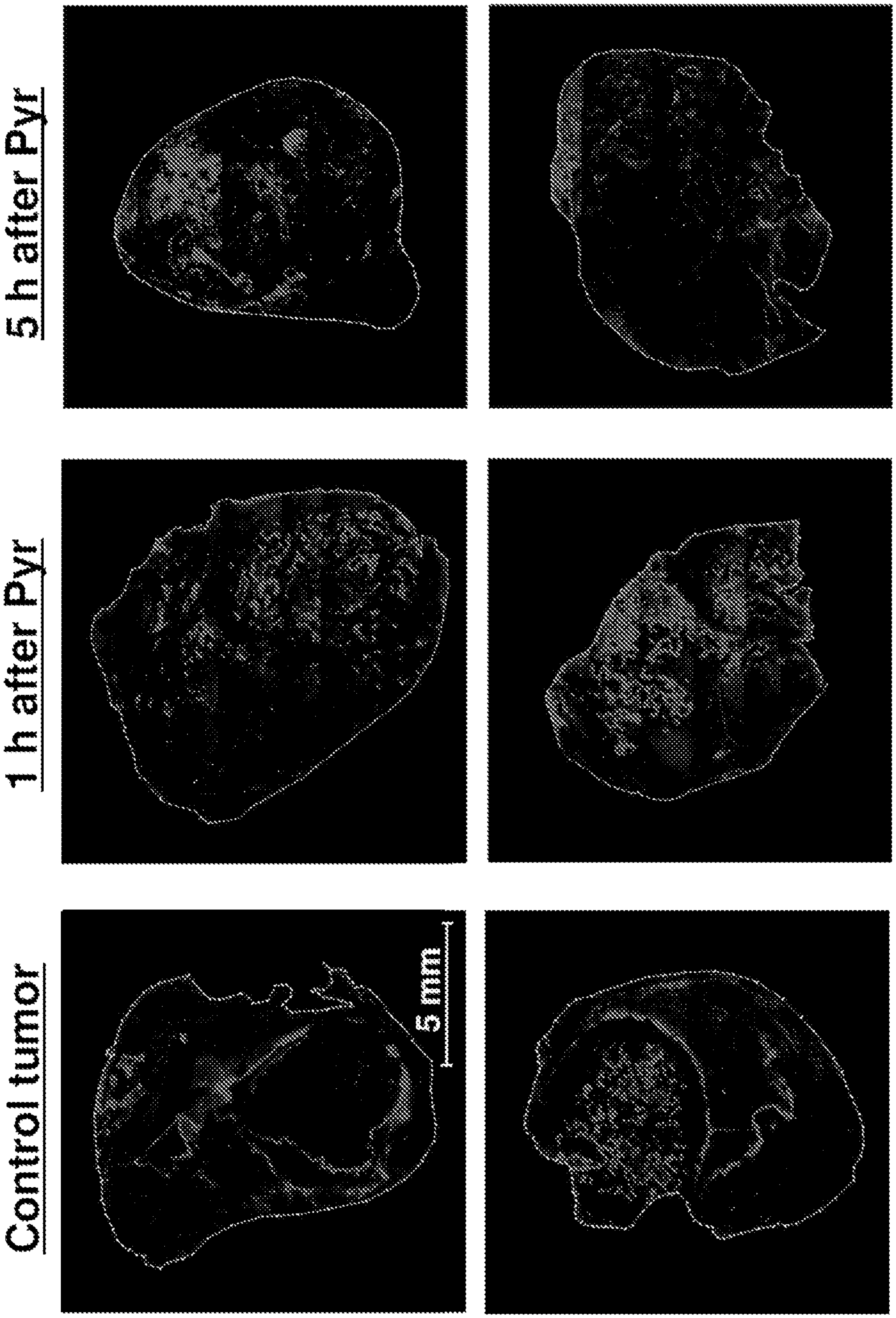
FIGS. 3A-3B are a series of digital images and a graph showing extent of hypoxia in tumors of control and pyruvate-treated mice.
Figure 3B:
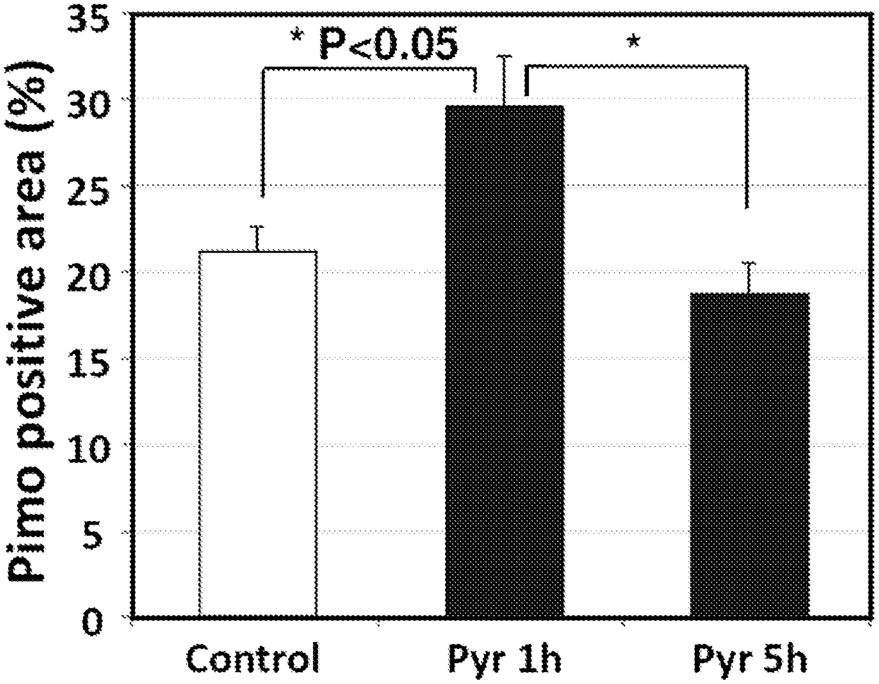

To independently confirm the changes in tumor $pO_2$ values in response to pyruvate administration, immunohistochemical assessment of tumor $pO_2$ using the hypoxia specific agent pimonidazole was carried out. The results showed increases in hypoxic fraction following pyruvate administration (FIGS. 3A and 3B). Pimonidazole positive area in tumors 1 hour after [1-$^{13}$C]pyruvate injection was significantly larger (29.5±2.9%) than control mice (21.1±1.4%), which did not receive [1-$^{13}$C]pyruvate injection (FIG. 3B). In agreement with $pO_2$ imaging results using EPRI, there was no difference in pimonidazole positive area between the tumors 5 hours after [1-$^{13}$C]pyruvate injection (18.7±1.8%) and the control tumors. The results of the EPRI and the immunohistochemical study indicate that tumor $pO_2$ is decreased by pyruvate administration, but the effect was transient.

Pyruvate-Induced Hypoxia Reduces Efficacy of Radiotherapy

Figure 4:
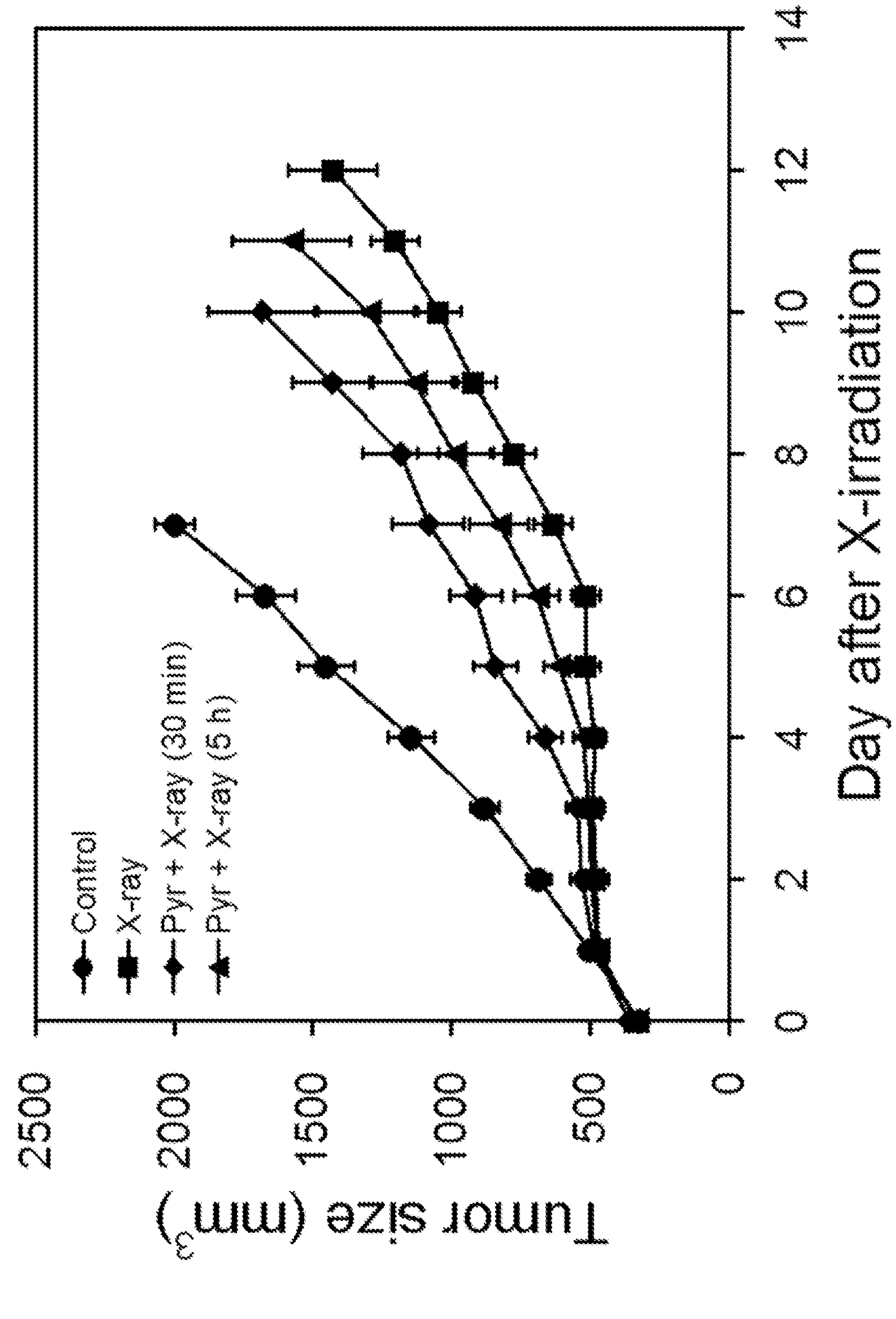
FIG. 4 is a graph showing tumor growth after X-irradiation in the presence or absence of [1-$^{13}$C]pyruvate-induced hypoxia. The control group (●, n=5) was neither X-irradiated nor administered [1-$^{13}$C]pyruvate. X-irradiations to the tumors were carried out without (■, n=5), 30 minutes after (♦, n=6), and 5 hours after (▲, n=7) [1-$^{13}$C]pyruvate injection.

Hypoxia is a critical factor that determines tumor resistance to radiotherapy and some kinds of chemotherapy. Although the pyruvate-induced hypoxia is transient, the decrease in oxygen concentration may limit the efficacy of cancer therapy, if the cancer treatments are provided immediately after MRI with hyperpolarized [1-$^{13}$C]pyruvate. To elucidate the effect of exogenously injected pyruvate on radiotherapy, tumor growth was monitored after X-irradiation with and without [1-$^{13}$C]pyruvate injection (FIG. 4). X-irradiation (12 Gy) without pyruvate administration suppressed the tumor growth for 6-7 days compared with non-treated control group which received neither X-irradiation nor pyruvate administration. When tumors were exposed to X-irradiation 30 minutes after [1-$^{13}$C]pyruvate injection, a delay in tumor growth of 3-4 days was observed, indicating that the tumor growth delay effect of X-irradiation was compromised by [1-$^{13}$C]pyruvate administration. Interestingly, the effect of pyruvate-induced decrease in tumor oxygenation on radiotherapy was observed even 5 hours after pyruvate injection, whereas tumor $pO_2$ almost recovered to the levels before pyruvate injection as shown in FIG. 2. Secondary mechanisms such as activation of hypoxia inducible transcription factor-1 signaling during the pyruvate-induced transient hypoxia might partially contribute to the long lasting effect of pyruvate on radiotherapy in addition to the direct effect of oxygen concentration at the time of radiation. Alternatively, such secondary mechanisms can also contribute a more sustained tumor response to hypoxia-sensitive cytotoxic agents even after tumor tissue hypoxia has returned to baseline levels.

Thus, injection of a bolus dose of pyruvate to tumor-bearing mice needed for hyperpolarized $^{13}$C imaging experiments can cause transient decrease in tumor $pO_2$, and this decrease in $pO_2$ weakens the tumor suppressive effect of X-irradiation. It should be noted that the pyruvate-induced hypoxia may provide a benefit if combined with hypoxic toxins. The dose of pyruvate used in this study is at the high end of doses commonly reported in the literature of hyperpolarized pyruvate studies. Secondly, a clinical dose would likely be about an order of magnitude less than the dose used in this study. Hyperpolarized [1-$^{13}$C]pyruvate is a promising tool for metabolically profiling the tumor and also in monitoring tumor progression and treatment response. However, when this technique is applied clinically with cancer therapies, it is important to take into account the transient microenvironmental change such as tumor oxygenation by pyruvate injection itself that may modulate the efficacy of treatments.

Example 2

In Vivo Administration of a $pO_2$ Lowering Agent in Pancreatic Tumor-Bearing Mice This example shows the effect of using a $pO_2$ lowering agent to decrease $pO_2$ levels in a tumor.

Tumor generation in mice, pyruvate injections, non-invasive EPR imaging, and co-registration of $pO_2$ images from EPRI with anatomic images from MRI were performed as described in Example 1. Human pancreatic solid tumors were formed by injecting cells of a pancreatic cell line subcutaneously into the right hind leg of athymic nude mice. Human pancreatic cell lines used were SU8686, MiaPaca, and HS766T.

Figure 5A:
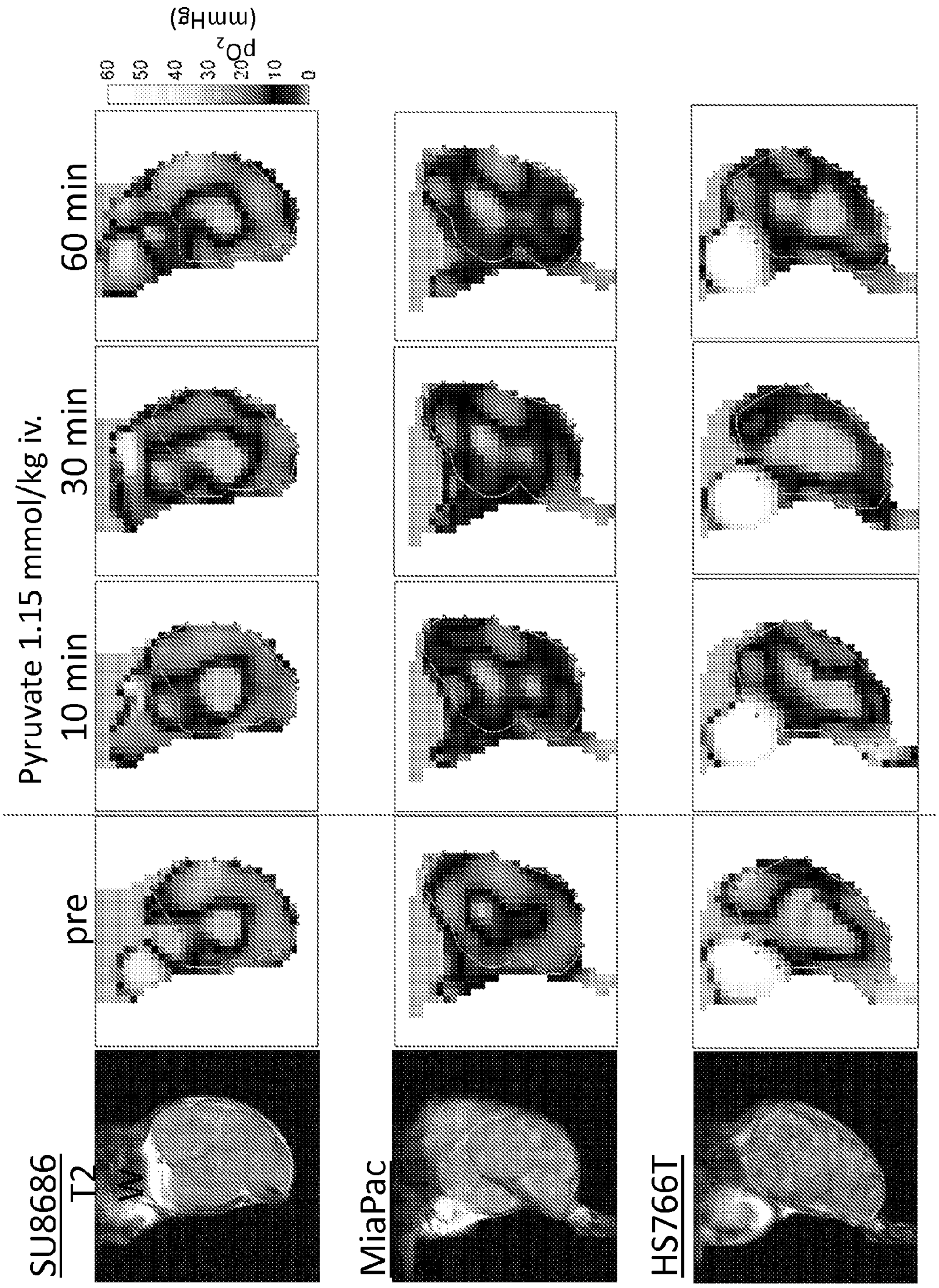
FIGS. 5A-5C are a series of digital images and graphs showing non-invasive monitoring of tumor $pO_2$ by EPRI and the effects of pyruvate injection.
Figure 5B:
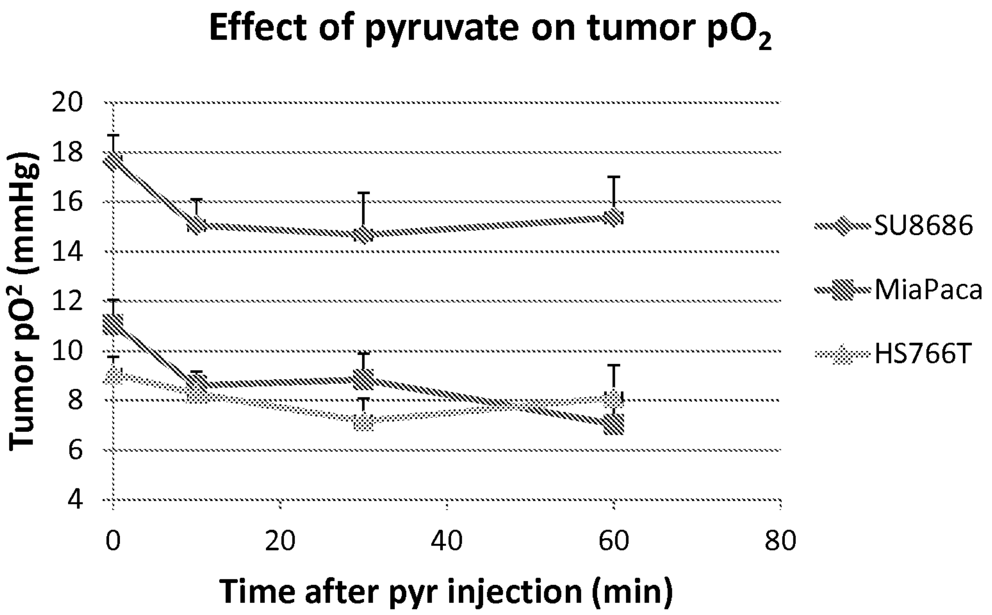
Figure 5C:
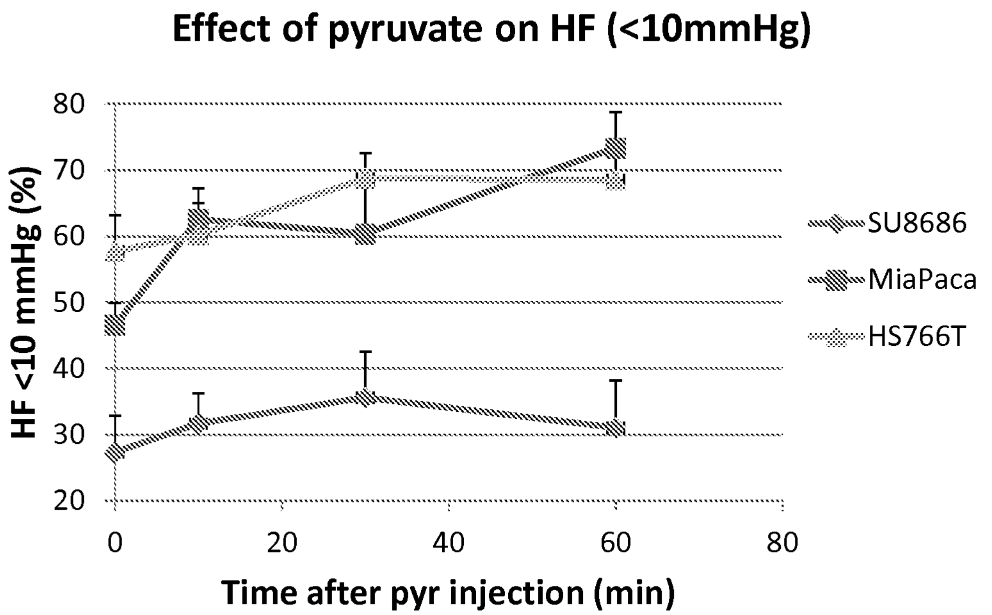

FIG. 5A shows $T_2$-weighted (T2W) anatomical images of three representative human pancreatic tumor-bearing mice, and the corresponding $pO_2$ maps measured before (pre), or 10 minutes, 30 minutes, and 1 hour after, [1-$^{13}$C]pyruvate injection (1.15 mmol/kg i.v.). $pO_2$ levels (0-60 mm Hg) in the tumors are correlated with shades of grey. FIG. 5B shows the effect of pyruvate on tumor $pO_2$ (n=5-6). FIG. 5C shows the effect of pyruvate on the hypoxic fraction (HF; $pO_2$<10 mmHg) in tumors (n=5-6). The data demonstrate that pyruvate can induce hypoxia in three pancreatic tumors.

Example 3

In Vivo Administration of a $pO_2$ Lowering Agent to Increase the Activity of a Hypoxia-Sensitive Agent and Delay Tumor Growth This example shows the effect of using a $pO_2$ lowering agent that transiently decreases the partial pressure of oxygen to increase the activity of a hypoxia-sensitive agent and delay tumor growth.

Experimental Methods

Figure 6A:
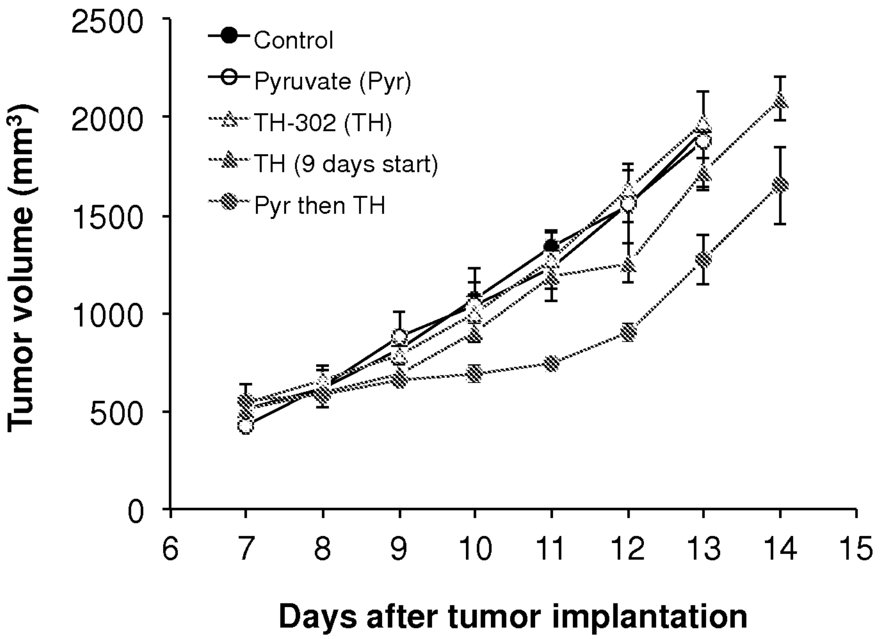
FIGS. 6A-6B are a series of graphs showing tumor growth in the presence of TH-302 alone or in combination with pyruvate.
Figure 6B:
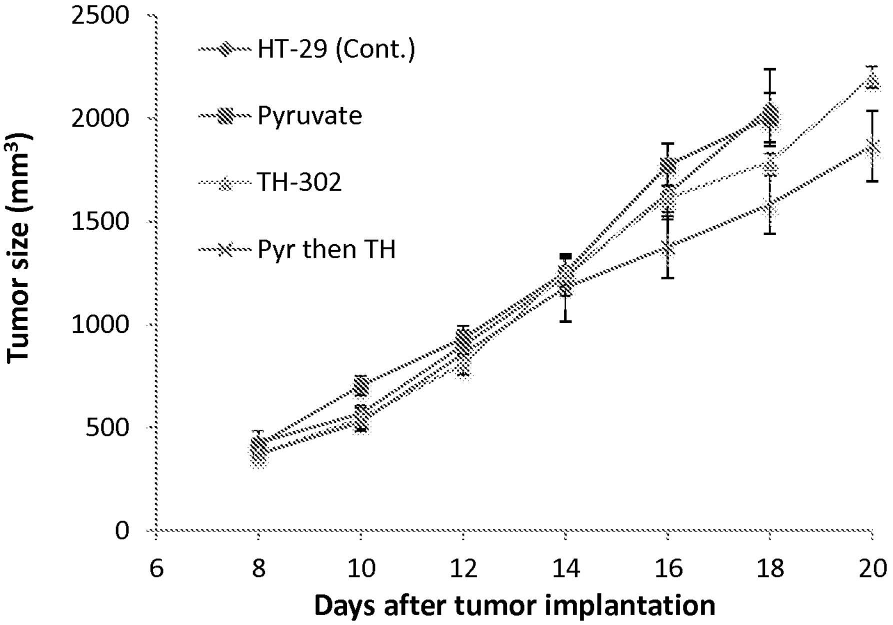

Mouse legs bearing tumors were prepared by subcutaneously injecting $5\times10^5$ SCCVII (mouse squamous cell carcinoma) cells or $1\times10^6$ HT29 (human colon cancer) cells to the hind leg of C3H or athymic nude mice, respectively. When tumor size became 400-500 mm$^3$, treatments were initiated. Mice were treated daily for 3 days with hypoxia-activated prodrug TH-302 (100 mg/kg/day, i.p.) alone, pyruvate (1.15 mmol/kg/day, i.v.) alone, or TH-302 injection 30 min. after pyruvate injection. Treatments were started on day 7 (SCCVII; FIG. 6A) or day 8 (HT29; FIG. 6B). In addition, some mice with SCCVII tumors did not receive TH-302 until day 9 (FIG. 6A). Tumor growth (volume/size in mm$^3$) was measured daily by caliper.

The data demonstrate that although pyruvate alone and TH-302 alone had a minor or small effect on SCCVII tumor growth when administered starting 7 days post-tumor implantation, the administration of pyruvate 30 minutes prior to TH-302 (combination therapy) significantly delayed SCCVII tumor growth (Table 1). Even when the start of TH-302 treatment was delayed until day 9 (▲; FIG. 6A) to allow the tumor to become more hypoxic, the delay in tumor growth was significantly greater as a result of the combination therapy, compared to TH-302 alone.

The data also demonstrate that the combination therapy induced a delay in HT29 tumor growth, compared to TH-302 alone (FIG. 6B and Table 1).

TABLE 1

| Period of time until tumor becomes 2-4 times original tumor size | | | | |
|---|---|---|---|---|
| | SCCVII (Days) | | HT29 (Days) | |
| | 2 times | 3 times | 3 times | 4 times |
| Non-treated | 3.0 | 5.2 | 7.2 | 8.0 |
| TH-302 | 3.4 | 5.4 | 6.8 | 8.4 |
| Pyr then TH-302 | 5.75 | 7.0 | 7.2 | 9.6 |

Thus, this example provides evidence that pyruvate can enhance the efficiency of the hypoxia-activated pro-drug TH-302 in vivo.

Example 4

Pyruvate Increases Oxygen Consumption Rate in Tumor Cells In Vitro

This example shows that administration of pyruvate transiently induces hypoxia by increasing oxygen consumption via an increase in mitochondrial aerobic respiration.

Figure 7A:
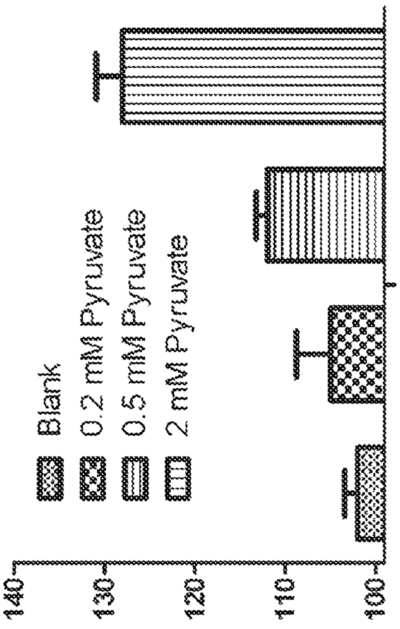
FIGS. 7A-7C are a series of graphs showing that pyruvate enhances mitochondrial oxygen consumption in SCCVII cells in vitro.
Figure 7B:
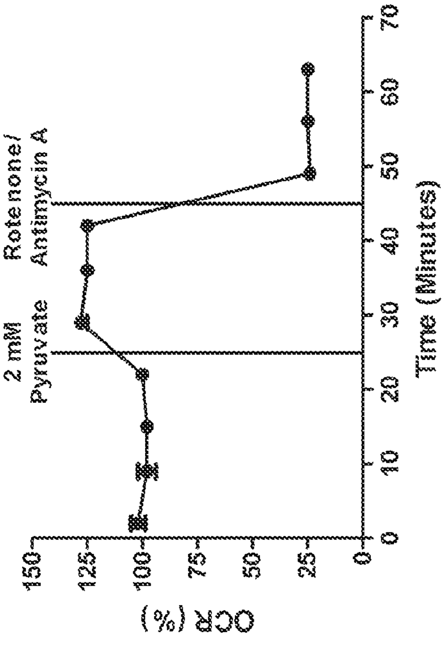
Figure 7C:
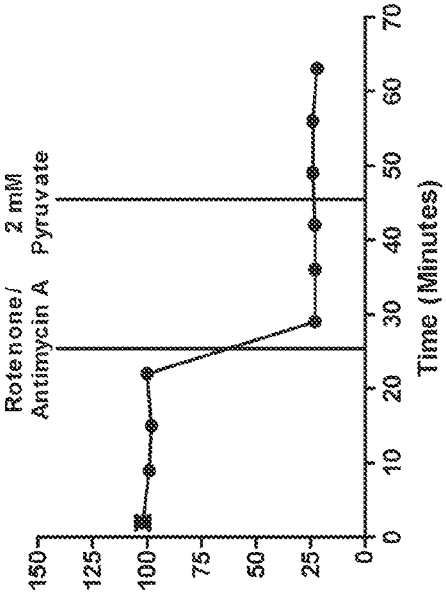

SCCVII cells were cultured in vitro in RPMI medium containing 10% fetal calf serum. FIG. 7A shows that oxygen consumption rate (OCR) increased in the SCCVII cells following incubation with various concentrations of pyruvate (0.2 mM, 0.5 mM, and 2 mM) for 21 minutes (data represent the percent change of OCR from baseline measurements). FIG. 7B shows the OCR in SCCVII cells treated with Rotenone/Antimycin A (oxidative phosphorylation complex 1 and complex 3 inhibitors, respectively) following 2 mM pyruvate treatment. FIG. 7C shows the OCR in SCCVII cells treated with Rotenone/Antimycin A prior to 2 mM pyruvate treatment. An increase in OCR when pyruvate is administered prior to treatment of the cells with Rotenone/Antimycin A demonstrates that the increase is dependent upon mitochondrial oxygen consumption. Thus, this example shows that pyruvate increases oxygen consumption by increasing mitochondrial aerobic respiration.

Example 5

Administration of a $pO_2$ Lowering Agent to Increase the Activity of a Hypoxia-Sensitive Agent This example shows methods of using a $pO_2$ lowering agent that decreases the partial pressure of oxygen to increase the activity of a hypoxia-sensitive agent.

Animals and Tumors

Tumor cells are maintained in vivo and in vitro. Tumor cell monolayers are harvested with 0.05% trypsin. From this suspension, cells are resuspended in medium and are inoculated intradermally in the back of each mouse at a site approximately 2 cm above the tail. Experiments are begun two weeks later when the mean tumor volume is approximately 200 $mm^3$.

Drugs

For animal studies, a hypoxia-sensitive agent, such as Tirapazamine (SR 4233) is dissolved in normal saline at a concentration of 1 mg/ml and injected intraperitoneally (i.p.) on a mmol/kg basis. An isotonic solution of a $pO_2$ lowering agent, for example pyruvate or succinate (pH 7.4), is prepared by dissolving the $pO_2$ lowering agent in an alkaline solution containing EDTA.

Cell Survival

For animal studies, tumor cell survival is evaluated according to an in vivo/in vitro excision assay. Toward this end, mice are sacrificed after treatment of the hypoxia-sensitive agent, either in the presence or absence of a $pO_2$ lowering agent. Tumors are excised, minced, and dissociated with an enzyme cocktail and cells are plated for a clonogenic assay. Resultant tumor cell colonies are stained with crystal violet and counted after two weeks incubation at 37° C. in a 5% $CO_2$ humidified atmosphere. Relative clonogenic cells per tumor is calculated as the product of plating efficiency and tumor cell yield for treated tumors relative to that for control untreated tumors assayed in parallel.

For the studies on cells in vitro, tumor cells are seeded into 60 mm glass petri dishes in medium supplemented with fetal bovine serum. The experiments are performed 4 to 5 days later. The growth medium is then replaced with 2 ml of medium without serum containing a hypoxia-sensitive agent. In each experiment, groups are included in which treatment with a $pO_2$ lowering agent and/or a hypoxia-sensitive agent are performed both simultaneously and with an interval between the treatments. Exposure to the $pO_2$ lowering agent and/or the hypoxia-sensitive agent is for one hour under hypoxic conditions. To achieve hypoxia, the dishes are loaded into gassing chambers and connected to a gassing manifold comprising a vacuum outlet line and inlet lines for air or nitrogen (+5% $CO_2$). After gassing, the chambers are sealed and incubated for one hour at 37° C. The oxygen level in the medium is measured using a Clarke electrode to show that hypoxia is achieved rapidly. Immediately after the treatment with the $pO_2$ lowering agent and/or hypoxia-sensitive agent, the cells are trypsinized, counted, and replated, and incubated for 14 days at 37° C. in a 5% $CO_2$ humidified atmosphere, after which the colonies are stained with crystal violet and counted.

The results show that both in vivo and in vitro there is a reduction in the number of colonies in the sample that was exposed to both the $pO_2$ lowering agent and the hypoxia-activated agent. Thus, a $pO_2$ lowering agent, such as pyruvate or succinate, increases the cytotoxicity activity of a hypoxia-sensitive agent both in vivo and in vitro.

Example 6

Method for Treating a Subject Having a Tumor

This example describes methods that can be used to treat a subject having a tumor. However, one skilled in the art will appreciate based on the teachings herein that methods that deviate from these specific methods can also be used to successfully treat a subject having a tumor.

In an example, a subject who has been diagnosed with a tumor is identified. Following subject selection, a therapeutically effective amount of a hypoxia-sensitive agent and a therapeutically effective amount of an oxygen partial pressure ($pO_2$) lowering agent are administered to the subject. In one specific, non-limiting example, a therapeutically effective amount of pyruvate (an amount sufficient to induce hypoxia in a tumor or increase the hypoxic fraction of a tumor) is administered to the subject prior to the administration of a therapeutically effective amount of a hypoxia-sensitive agent. The amount of the $pO_2$ lowering agent and the hypoxia-sensitive agent administered to prevent, reduce, inhibit, and/or treat the tumor depends on the subject being treated, the severity of the disorder, and the manner of administration of the therapeutic composition. Ideally, a therapeutically effective amount of a hypoxia-sensitive agent is the amount sufficient to prevent, reduce, and/or inhibit, and/or treat the condition (e.g., a tumor) in a subject without causing a substantial cytotoxic effect in the subject.

A reduction in the clinical symptoms associated with the tumor, for example, decreased tumor volume or size, indicates the effectiveness of the treatment.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for enhancing the efficacy of a hypoxia activated prodrug in a subject having a tumor, comprising administering to the subject a therapeutically effective amount of the hypoxia activated prodrug and a therapeutically effective amount of $CH_3COCOO^-$, $^{13}CH_3COCOO^-$, and/or $CH_3COCOOH$, wherein the amount of the $CH_3COCOO^-$, $^{13}CH_3COCOO^-$, and/or $CH_3COCOOH$, administered is sufficient to transiently enhance hypoxia of the tumor, wherein the hypoxia activated prodrug is phosphorodiamidic acid (TH-302), and wherein the tumor is a pancreatic cancer, a colon cancer or a squamous cell carcinoma, thereby enhancing the efficacy of the hypoxia activated prodrug in the subject.

2. The method of claim 1, wherein the tumor is the squamos cell carcinoma.

3. The method of claim 1, wherein the $CH_3COCOO^-$, $^{13}CH_3COCOO^-$, and/or $CH_3COCOOH$, decreases the oxygen partial pressure in the tumor.

4. The method of claim 1, wherein the $CH_3COCOO^-$, $^{13}CH_3COCOO^-$ and/or $CH_3COCOOH$, is administered in a single dose.

5. The method of claim 1, wherein the $CH_3COCOO^-$, $^{13}CH_3COCOO^-$, and/or $CH_3COCOOH$, is administered in multiple doses.

6. The method of claim 1, wherein the $CH_3COCOO^-$, $^{13}CH_3COCOO^-$, and/or $CH_3COCOOH$, is administered prior to administering the hypoxia activated prodrug.

7. The method of claim 1, wherein the $CH_3COCOO^-$, $^{13}CH_3COCOO^-$, and/or $CH_3COCOOH$, is administered concurrently with the hypoxia activated prodrug.

8. The method of claim 1, further comprising measuring the partial pressure of oxygen in the tumor after administration of $CH_3COCOO^-$, $^{13}CH_3COCOO^-$ and $CH_3COCOOH$, and detecting a decrease in the partial pressure of oxygen.

9. The method of claim 1, wherein the tumor is the colon cancer.

10. The method of claim 1, comprising administering to the subject a therapeutically effective amount of $CH_3COCOO^-$ or $^{13}CH_3COCOO^-$.

11. The method of claim 2, wherein the cancer is the pancreatic cancer.

12. A method for treating a tumor in a subject, comprising administering to the subject a therapeutically effective amount of phosphorodiamidic acid (TH-302); and administering to the subject a therapeutically effective amount of $CH_3COCOOH$, $CH_3COCOO^-$, or $^{13}CH_3COCOO^-$ wherein the therapeutically effective amount is sufficient to transiently enhance hypoxia of the tumor, thereby enhancing the efficacy of phosphorodiamidic acid (TH-302) and treating the tumor in the subject, wherein the tumor is pancreatic cancer, colon cancer or squamous cell carcinoma, and wherein treating the tumor comprises reducing growth of the tumor.

13. The method of claim 12, wherein the tumor is the pancreatic cancer.

14. The method of claim 12, wherein the tumor is the squamous cell carcinoma.

15. The method of claim 12, comprising administering to the subject the therapeutically effective amount of $^{13}CH_3COCOO^-$.

16. The method of claim 12, comprising administering to the subject the therapeutically effective amount of $CH_3COCOO^-$.

17. The method of claim 12, wherein the tumor is the colon cancer.

* * * * *